US009541503B2

(12) United States Patent
Stoll et al.

(10) Patent No.: US 9,541,503 B2
(45) Date of Patent: Jan. 10, 2017

(54) COMPACT SYSTEMS, COMPACT DEVICES, AND METHODS FOR SENSING LUMINESCENT ACTIVITY

(71) Applicant: Avago Technologies General IP (Singapore) Pte. Ltd., Singapore (SG)

(72) Inventors: Lothar Stoll, Munich (DE); Martin Weigert, Etterzhausen/Bavaria (DE); Detlef Bernd Krabe, Munich (DE)

(73) Assignee: Avago Technologies General IP (Singapore) Pte. Ltd., Singapore (SG)

( * ) Notice: Subject to any disclaimer, the term of this patent is extended or adjusted under 35 U.S.C. 154(b) by 14 days.

(21) Appl. No.: 14/523,880

(22) Filed: Oct. 25, 2014

(65) Prior Publication Data

US 2016/0011111 A1 Jan. 14, 2016

Related U.S. Application Data

(63) Continuation-in-part of application No. 14/330,022, filed on Jul. 14, 2014.

(51) Int. Cl.
  *G01N 21/64* (2006.01)
  *H01L 25/00* (2006.01)
  (Continued)

(52) U.S. Cl.
  CPC ......... *G01N 21/645* (2013.01); *H01L 21/568* (2013.01); *H01L 25/167* (2013.01); *H01L 25/50* (2013.01); *H01L 31/02002* (2013.01); *H01L 31/0203* (2013.01); *H01L 31/12* (2013.01); *G01N 2201/0221* (2013.01); *H01L 23/3107* (2013.01); *H01L 23/3121* (2013.01);
  (Continued)

(58) Field of Classification Search
  None
  See application file for complete search history.

(56) References Cited

U.S. PATENT DOCUMENTS

| 4,713,841 A | 12/1987 | Porter et al. |
| 7,048,450 B2 | 5/2006 | Beer et al. |

(Continued)

OTHER PUBLICATIONS

W.R. Bottoms & William T. Chen, "A Description of What Will Specifically be Needed to Support the Continuation of the Rapid Pace of Progress Achieved by the Electronics Industry," ITRS Chapter: Assembly & Packaging, Future , Jan. 12, 2012, 8 pages, Fab International Issue 40, Future Fab International, http://www.future-fab.com.

(Continued)

*Primary Examiner* — Yasser A Abdelaziez

(57) ABSTRACT

Compact systems, compact devices and methods are provided to sense changes in luminescence due to environmental influences on a luminescent material. Such systems, devices and methods may be implemented in a compact device, e.g., an integrated circuit package, which may be incorporated into or attached to a device, such as a smartphone, watch, flashlight, vehicle, etc. The systems, devices, and methods described herein are useful in sensing luminescence, as well as changes in luminescence that are indicative of environmental influences, such as the presence and concentration of a gas or chemical, ambient temperature, pressure, light, etc., in an area surrounding a luminescent material included in a compact device.

27 Claims, 16 Drawing Sheets

(51) Int. Cl.
    *H01L 25/16*    (2006.01)
    *H01L 21/56*    (2006.01)
    *H01L 31/02*    (2006.01)
    *H01L 31/0203*  (2014.01)
    *H01L 31/12*    (2006.01)
    *H01L 23/31*    (2006.01)

(52) U.S. Cl.
    CPC ....... *H01L 2224/11* (2013.01); *H01L 2224/18* (2013.01); *H01L 2224/48247* (2013.01)

(56) References Cited

U.S. PATENT DOCUMENTS

| | | | |
|---|---|---|---|
| 7,170,049 B2 | 1/2007 | Iwanczyk et al. | |
| 7,536,066 B2 | 5/2009 | Kato et al. | |
| 7,833,480 B2* | 11/2010 | Blazewicz | G01N 21/6408 250/458.1 |
| 8,064,739 B2 | 11/2011 | Binkert et al. | |
| 8,352,009 B2 | 1/2013 | Hoarau et al. | |
| 8,642,385 B2 | 2/2014 | Xue et al. | |
| 8,642,397 B1 | 2/2014 | Gong et al. | |
| 8,742,370 B2 | 6/2014 | Tkachuk | |
| 2002/0095077 A1* | 7/2002 | Swedlow | A61B 5/14551 600/323 |
| 2004/0259282 A1 | 12/2004 | Oohata | |
| 2008/0122122 A1 | 5/2008 | Wong et al. | |
| 2008/0186702 A1 | 8/2008 | Camras et al. | |
| 2010/0316184 A1 | 12/2010 | Iwanczyk et al. | |
| 2013/0001795 A1 | 1/2013 | Lim et al. | |
| 2013/0237774 A1 | 9/2013 | Schentag et al. | |
| 2013/0264684 A1 | 10/2013 | Yu et al. | |
| 2013/0320471 A1 | 12/2013 | Luan | |

OTHER PUBLICATIONS

W.R. Bottoms & William T. Chen, "An Overview of the Innovations, Emerging Technologies and Difficult Challenges Regarding the Assembly & Packaging Chapter of the ITRS," Assembly & Packaging, Jan. 15, 2009, 4 pages, Future Fab International Issue 28, Future Fab International, http://www.future-fab.com.
Wafer Level Chip Scale Package (WLCSP), Freescale Semiconductor Application Note, Aug. 2009, 16 pages, AN3846, Rev. 2.0.
eWLB Embedded Wafer-Level Ball Grid Array, Aug. 2011, p. 1-2, STATS chipPAC ltd. Singapore, www.statschippac.com.
Kitronik Ltd, "5mm RGB LED Common Anode," Technology Data Sheet & Specifications, http://www.kitronik.co.uk, 3 pages.
Siliconcore Technology, "SiliconCore LED Products," www.silicon-core.com, SiliconCore Technology Inc, Jan. 4, 2013, 53 pages.
Thingm Labs, "Blinkm Datasheet," blinkm.thingsm.com, V20100810, Thingm Labs, Pasadena, CA, 50 pages.
Dr. William Henry, "MicroLEDs Enabling New Generation of Fluorescence Instruments," BioPhotonics, www.photonics.com, 2014, 5 pages.
Artur Dybko, "Fiber Optic Chemical Sensors," Chemical Sensors Research Group, 2005, 9 pages, http://csrg.ch.pw.edu.pl/tutorials/fiber.
"Renesas to Commercialize FO-WLP Technology in MCU Product Line by 2011," /-Micronews, Advanced Packaging, Oct. 10, 2010, http://www.renesas.com.

* cited by examiner

COMPACT SYSTEMS, COMPACT DEVICES, AND METHODS FOR SENSING LUMINESCENT ACTIVITY

CROSS-REFERENCE TO RELATED APPLICATIONS

This application is a continuation-in-part of U.S. application Ser. No. 14/330,022, filed Jul. 14, 2014, entitled "METHODS FOR PERFORMING EMBEDDED WAFER-LEVEL PACKAGING (eWLP) AND eWLP DEVICES, PACKAGES AND ASSEMBLIES MADE BY THE METHODS," which is a continuation-in-part application of U.S. application Ser. No. 14/213,342, filed Mar. 14, 2014, entitled "METHODS FOR PERFORMING EXTENDED WAFER-LEVEL PACKAGING (eWLP) AND eWLP DEVICES MADE BY THE METHODS," both of which are currently pending and both of which are incorporated herein by reference in their entireties.

TECHNICAL FIELD

The invention relates to detection of luminescent activity. More particularly, the invention relates to sensing luminescent activity using a compact optoelectronic device.

BACKGROUND

Luminescence is the emission of light by a substance that does not result from heat. Luminescence may be caused by chemical reactions, electrical energy, subatomic motions, stress on a crystal, etc.

Luminescent materials, such as fluorescent materials, phosphorescent materials, and bioluminescent materials, naturally emit light at a particular wavelength. Environmental influences affect the intensity of the light emitted by luminescent materials. In particular, certain environmental influences, such as the presence of gases, cause the intensity of light emitted by certain luminescent materials to decrease.

While there are systems available for detecting a change in the illumination of light emitted by luminescent materials due to environmental influences, such systems typically require a chamber enclosing a luminescent material, a light source, and a light detector. Detection of an environmental influence, such as a gas, on the luminescent material is detected within the chamber. Such systems are complicated and cumbersome to use. Such systems also are relatively large in size and are therefore limited to use in larger form factor applications where their size can be accommodated.

A need exists for compact systems, compact devices, and methods for sensing luminescence due to environmental influences that are easy to use.

SUMMARY

The invention is directed to compact systems, compact devices, packages, and methods for sensing luminescent activity. In accordance with an illustrative embodiment, the compact system comprises an optoelectronic module and a luminescence module. The optoelectronic module includes a light source configured to emit light at a predetermined wavelength and a wavelength selective light detector configured to detect light within a predetermined wavelength range. The luminescence module includes a luminescent material. The luminescence module is configured to emit light at a variable wavelength that is different from the predetermined wavelength responsive to the light emitted by the light source that is incident on the luminescent material. An intensity of the light emitted by the luminescence module depends upon at least one environmental influence on the luminescent material in an area surrounding the compact system. The wavelength selective light detector is configured to detect the light emitted by the luminescence module that is within a predetermined wavelength range and to emit a value corresponding to the intensity of the light emitted by the luminescence module.

In accordance with another illustrative embodiment, the compact device comprises a light source and a wavelength selective light detector. The light source is configured to emit light at a predetermined wavelength. The wavelength selective light detector is configured to detect light within a predetermined wavelength range. A luminescence module including a luminescent material is configured to emit light at a variable wavelength that is different from the predetermined wavelength responsive to the light emitted by the light source that is incident on the luminescent material, and an intensity of the light emitted by the luminescence module depends upon at least one environmental influence on the luminescent material in an area surrounding the compact device. The wavelength selective light detector detects the light emitted by the luminescence module that is within a predetermined wavelength range and emits a value corresponding to the intensity of the light emitted by the luminescence module.

In accordance with an illustrative embodiment, the method comprises the following: emitting, by a light source, light at a predetermined wavelength; absorbing, by a luminescence module including a luminescent material, the light emitted by the light source that is incident on the luminescent material; emitting, by the luminescence module, light at a variable wavelength that is different from the predetermined wavelength; detecting, by a wavelength selective light detector, the light emitted by the luminescence module that is within a predetermined wavelength range; and emitting a value corresponding to the intensity of the light emitted by the luminescence module, wherein the light source, the luminescence module, and the wavelength selective light detector are included in a compact device, and an intensity of the light emitted by the luminescence module depends upon at least one environmental influence on the luminescent material in an area surrounding the compact device.

In accordance with another illustrative embodiment, the method is an embedded Wafer-Level Packaging (eWLP) method is used to form a compact optoelectronic package for sensing luminescent activity. The method comprises: forming an eWLP artificial wafer comprising a plurality of first and second chips, a luminescent material carrier, and a luminescent material disposed in or on the luminescent material carrier; forming an electrical interface on one or both of a front side and a back side of the eWLP artificial wafer; and dicing the eWLP wafer into a plurality of eWLP packages. Each of the first chips and the second chips has at least a first light source formed therein and a first wavelength selective light detector formed therein, respectively. Each eWLP package includes at least one of the first chips, one of the second chips, a portion of the luminescent material carrier, and a portion of the luminescent material. Each of the first light sources is configured to emit light at a predetermined wavelength. The luminescent material emits light at a variable wavelength that is different from the predetermined wavelength responsive to the light emitted by the first light source that is incident on the luminescent material. The first wavelength selective light detector is configured to detect light emitted by the luminescent material that is within a predetermined wavelength range and to emit a value corresponding to an intensity of the light emitted by the luminescent material.

In accordance with another illustrative embodiment, the compact optoelectronic package is an embedded Wafer-Level Packaging (eWLP) package diced from an eWLP artificial wafer. The eWLP package comprises first and second chips, a luminescent material carrier, and a luminescent material disposed in or on the luminescent material carrier. The first and second chips have at least a first light source and a first wavelength selective light detector formed therein, respectively. The first light source is configured to emit light at a predetermined wavelength. The luminescent material is configured to emit light at a variable wavelength that is different from the predetermined wavelength responsive to the light emitted by the first light source that is incident on the luminescent material. The first wavelength selective light detector is configured to detect light emitted by the luminescent material that is within a predetermined wavelength range and to emit a value corresponding to an intensity of the light emitted by the luminescent material. An electrical interface is disposed on one or both of a front side and a back side of the eWLP package. The eWLP package includes a carrier on which the eWLP package is mounted. The carrier has an electrical interface that is interfaced with the electrical interface of the eWLP package.

These and other features and advantages of the invention will become apparent from the following description, drawings and claims.

DETAILED DESCRIPTION OF ILLUSTRATIVE EMBODIMENTS

Embodiments of the invention include systems, devices and methods for sensing luminescent activity. Such systems, devices and methods may be implemented in a compact device, e.g., an integrated circuit, which may be incorporated into or attached to a device, such as a smartphone, watch, flashlight, vehicle, etc. The systems, devices, and methods described herein are useful in sensing luminescence, as well as changes in luminescence that are indicative of environmental influences, such as the presence and concentration of a gas or chemical, ambient temperature, pressure, light, etc., in an area surrounding a luminescent material included in a compact device.

Figure 1:
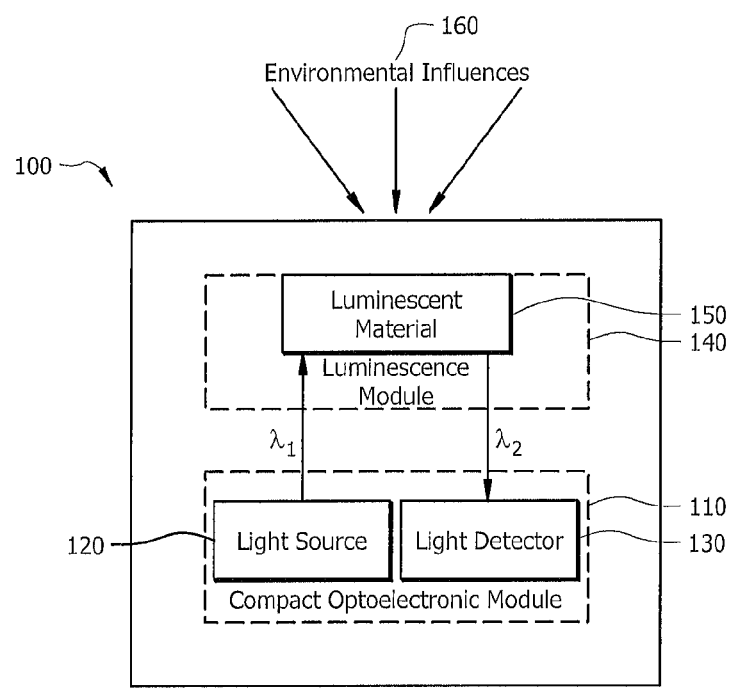
FIG. 1 illustrates a compact system for sensing luminescence in accordance with an illustrative embodiment.

FIG. 1 illustrates a compact system for sensing luminescence in accordance with an illustrative embodiment. As shown in FIG. 1, the system 100 includes an optoelectronic module 110 and a luminescence module 140. According to an illustrative embodiment, the optoelectronic module 110 and the luminescence module 140 may be integrated into a compact device having a size that is 4 to 9 mm$^2$ in some cases and as small as 1 to 2 mm$^2$ in some cases. The size of this system makes it easy to use in many different environments for the sensing of luminescent activity due to many different environmental influences without the need for an enclosure chamber.

Referring again to FIG. 1, the optoelectronic module 110 includes a light source 120 which emits light at a predetermined excitation wavelength $\lambda_1$ (or waveband $\Delta\lambda_1$). For illustrative purposes, the light source 120 described herein is an electrical-to-optical converter, such as a light emitting diode (LED), which converts an electrical signal into light. While described herein as an LED, it should be appreciated that the light source 120 may be implemented with any suitable light source emitting light at the wavelength $\lambda_1$ (or waveband $\Delta\lambda_1$), such as a super luminescent diode (SLED), a vertical cavity surface emitting laser (VCSEL), etc.

The luminescence module 140 includes a luminescent material 150 upon which the light emitted from the light source 120 is incident. The luminescent material 150 absorbs the light from the light source 120. Responsive to the absorbed light from the light source 120 and environmental influences in the area surrounding the compact system 100 on the luminescent material 150, the luminescent material 150 emits light at a variable emission wavelength $\lambda_2$, where $\lambda_1 < \lambda_2$. The emitted light is, in turn, emitted by the luminescence module 140.

The optoelectronic module 110 also includes a wavelength selective light detector 130 for detecting light within a predetermined wavelength range. According to an illustrative embodiment, the predetermined wavelength range may be selected to detect light of a wavelength longer than the light emitted by the light source 120.

According to an illustrative embodiment, the wavelength selective light detector 130 is an optical-to-electrical converter, such as a photodiode (PD), which detects light and converts the light into an electrical signal. The wavelength selective behavior of the light detector 130 may be achieved either by a wavelength selective coating or by intrinsic principles of the detector, e.g. a band gap.

The wavelength selective light detector 130 detects light that is emitted by the luminescent material 150 in the presence of one or more environmental influences. The environmental influences may affect the intensity of the light emitted by the luminescent material. In particular, the degree to which the environmental influences are present, e.g., the concentration of the environmental influences, in the area surrounding the compact system 100 may affect the intensity of the light emitted by the luminescent material.

According to an illustrative embodiment, if light within the predetermined wavelength range is not detected from the luminescence module 140, this may be indicative of a high concentration or degree of presence of the one or more particular environmental influences on the luminescent material 150. For example, if there is a high concentration of a particular gas in the area surrounding the compact system 100, and the gas strongly affects the emission of light by the luminescent material 150, the luminescent material 150 may not emit light of a detectable intensity.

While described herein as PD, it should be appreciated that the light detector 130 may be implemented with any suitable wavelength selective light detector which detects light within a predetermined wavelength range, such as any suitable wavelength selective semiconductor light detector, e.g., an ambient light photo detector (APD), a silicon photomultiplier (SiPM) detector, etc., where the wavelength of the emitted light from the light source 120 is shorter than the wavelength of the detected light.

Although not shown in the interest of simplicity of illustration, it should be appreciated that the additional electronics may be integrated in the optoelectronic module 110. Such elements may be monolithically integrated with the light detector 130 and/or the light source 120 or may be implemented as a separate unit of the optoelectronic module 110. These electronics may include, e.g., amplifiers, phase comparators (described in further detail below), etc.

As explained above, the wavelength selective light detector 130 detects light emitted by the luminescence module 140 that is within the predetermined wavelength range. The wavelength selective light detector 130 outputs a value corresponding to the intensity of the detected light emitted by the luminescence module 140. According to one embodiment, the value may be a current value. According to another embodiment, the value may be a voltage value. The voltage value may be produced by using a transimpedance amplifier incorporated within the optoelectronic module 110 to convert the current value to a voltage value.

According to an illustrative embodiment, the current value or voltage value output by the wavelength selective light detector 130 is an indication of the concentration or degree of presence of one or more environmental influences on the luminescent material 150. If the light emitted by the luminescence module 140 is of such a low intensity that it cannot be detected by the wavelength selective light detector 130, this may be indicative of an extreme concentration or degree of presence of one or more environmental influences 160 in the area surrounding the luminescent material 150 included in the compact system 100. These environmental influences may cause the luminescent material 150 not to emit light at all or to emit light of such a low intensity that it cannot be detected by the wavelength selective light detector 130.

According to an illustrative embodiment, if no light is detected within the predetermined range by the wavelength selective light detector 130, the wavelength selective light detector 130 may output a current or voltage value that triggers an alarm. According to an illustrative embodiment, to cause an alarm to be generated, the light detector 130 may be an analog photodetector that transmits an electrical current or voltage signal corresponding to the intensity of the detected light to external circuitry (not shown for simplicity of illustration). If the intensity of the light detected is reduced, the output current or voltage value may also be reduced. The external circuitry may be calibrated to certain levels of current or voltage output, such that the external circuitry triggers an alarm if the current or voltage output is reduced to a particular current/voltage threshold level. There may be multiple alarms and multiple current/voltage threshold, such that one alarm may be generated if the current/voltage output is reduced to a first level and another alarm may be generated if the current/voltage output is reduced to second level, e.g., a current level less than the first current level.

According to another embodiment, the light detector 130 may be an integrated digital photodetector that outputs a digital signal to external circuitry responsive to light detection. Thus, for the example, the light detector may output a logic "1" if light is detected, and a logic "0" if light is not detected. Responsive to receipt of the logic "0", the external circuitry may generate an alarm. It should be appreciated that the light detector may, instead, output a logic "1" if light is not detected and a logic "0" if light is detected. In this case, the external circuitry would generate an alarm responsive to receipt of the logic "1".

As an illustrative example, consider a light source 120 that emits light at a wavelength within a blue wavelength spectrum (approximately 440 nm-500 nm). In the presence of an environmental influence, such as a gas, the luminescent material 150 absorbs the blue light and emits light at a wavelength within a red wavelength spectrum (approximately 625-740 nm). Assuming that the red light is at a wavelength that is within the predetermined wavelength range of the wavelength selective light detector 130 and the red light emitted is of a detectable intensity, the red light would be detected. The light detector 130 may output a current or voltage having a value corresponding to the intensity of the detected red light.

Following the illustrative example, if the luminescent material 150 is in the presence of a gas which affects the emission of light to such an extent that the luminescent material 150 does not emit light of a detectable intensity, the wavelength selective light detector 130 would not detect light emitted by the luminescence module 140. In this case, the wavelength selective light detector 130 may output a current or voltage signal having a value that may, in turn, trigger an alarm.

Figure 2:
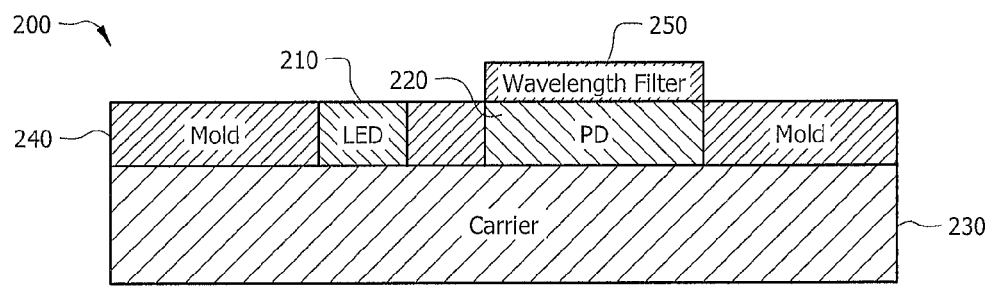
FIG. 2 illustrates in detail an optoelectronic module in accordance with an illustrative embodiment.

FIG. 2 illustrates in detail an optoelectronic module 200 in accordance with an illustrative embodiment. As shown in FIG. 2, an optoelectronic module 200 includes a carrier 230, such as a wafer, upon which a light source, e.g., a light emitting diode (LED) 210, and a wavelength selective light detector, e.g., a photodetector PD 220, are held in place via a mold 240 having electrical connections.

A wavelength filter 250 filters the light emitted by the LED 210 from the PD 220. Referring to the illustrative example above, the wavelength filter 250 filters out the red light emitted by the LED 210 from detection by the PD. The wavelength selective filter 250 may be implemented with a coating that may serve as an interference layer, an absorption layer, a photonic layer, etc. The coating may be applied by printing the coating as an adhesive layer or by molecular depletion processes, e.g., sputtering, evaporation, etc. If wavelength selectivity is achieved by a photonic layer, the generation of the layers can be part of the integrated circuit manufacturing process. The wavelength selective coating may be structured so only the PD 220 is covered. Structuring of the wavelength selective coating may be performed during the application process, e.g., by masking or lift off, or, if a planar depletion is applied, after depletion, e.g., by etching.

Figure 3:
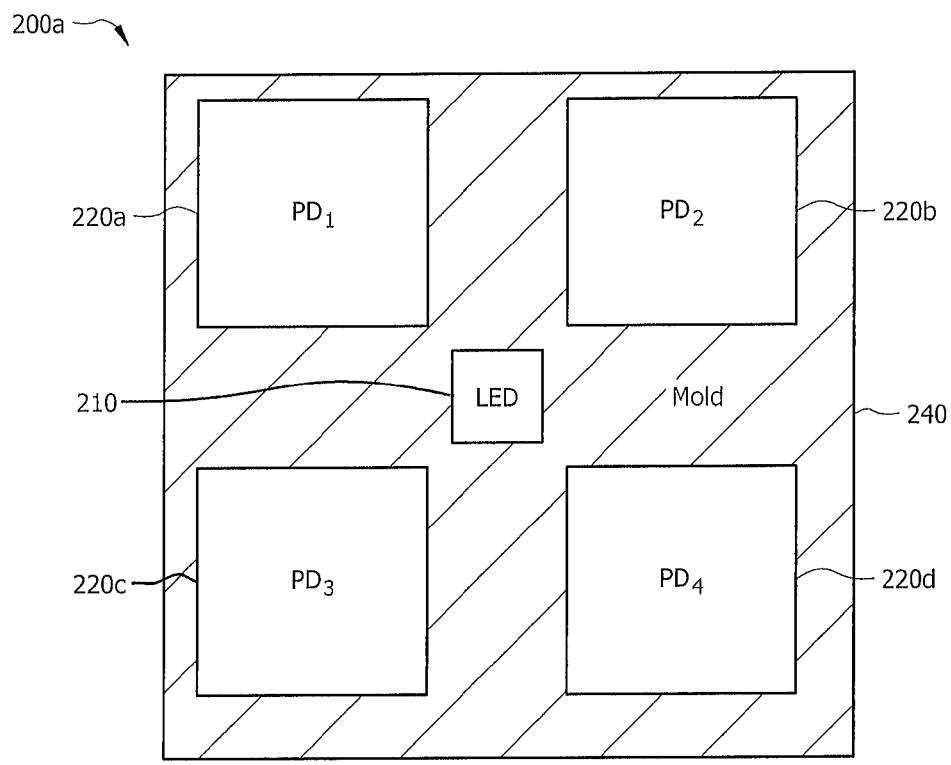
FIG. 3 illustrates an optoelectronic module including multiple wavelength selective light detectors according to an illustrative embodiment.

FIG. 3 illustrates an optoelectronic module 200a including multiple wavelength selective light detectors according to an illustrative embodiment. The optoelectronic module 200a is similar to the optoelectronic module 200, except that the optoelectronic module 200a includes multiple wavelength selective light detectors 220a, 220b, 220c, and 220d. Each of the wavelength selective light detectors 220a, 220b, 220c, and 220d detects light within a different respective predetermined wavelength range. According to one embodiment, at least one of the wavelength selective light detectors 220a, 220b, 220c and 220d may be sensitive to the output wavelength of the light source and can be used as a monitor diode.

According to an illustrative embodiment, the detection of light by one or more of the wavelength selective light detectors 220a, 220b, 220c and 220d may indicate the concentration or degree of presence of one or more particular environmental influences on the luminescent material (not shown in FIG. 3 for simplicity of illustration). The intensity of the light detected by one or more of the wavelength selective light detectors 220a, 220b, 220c, and 220d may be indicative of a particular concentration or degree of presence of one or more environmental influences surrounding the luminescent material.

As an illustrative example, assume that the predetermined wavelength ranges of the wavelength selective light detectors 220a and 220b are selected so that they detect light emitted from the luminescent material in the absence of particular concentrations of $CO_2$ and CO, respectively, on the luminescent material. If the concentration of $CO_2$ or CO surrounding the luminescent material is a particular amount, this will affect the luminescent material such that it may not emit light of a detectable intensity within the predetermined wavelength ranges of the wavelength selective light detectors 220a and 220b. However, the luminescent material may still emit light detectable by the wavelength selective light detectors 220c and 220d. In this case, each of the light detectors 220a, 220b, 220c and 220d may output a current or voltage signal having a value corresponding to the intensity of detected light. However, the wavelength selective light detectors 220a and 220b may output current or voltage signals having values that meet a predetermined threshold, indicating the presence of the particular concentrations of $CO_2$ and CO, respectively. This may, in turn, cause one or more alarms to be triggered.

Figure 4:
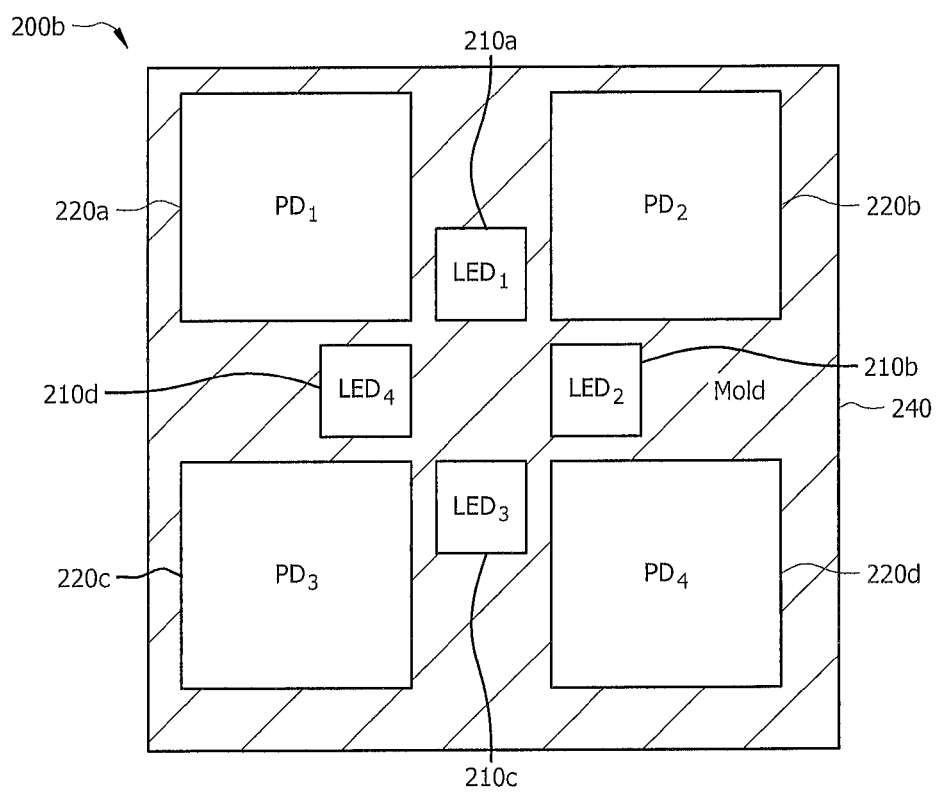
FIG. 4 illustrates an optoelectronic module including multiple light sources and multiple wavelength selective light detectors according to an illustrative embodiment.

FIG. 4 illustrates an optoelectronic module 200b including multiple light sources and multiple wavelength selective light detectors according to an illustrative embodiment. The optoelectronic module 200b is similar to the optoelectronic module 200a, except that the optoelectronic module 200b includes multiple light sources 210a, 210b, 210c, and 210d. Each of the light sources 210a, 210b, 210c and 210d emits light at a different respective predetermined emission wavelength. The light emitted from the light sources 210a, 210b, 210c and 210d is absorbed by the luminescent material, and the luminescent material, in turn, emits light at excitation wavelengths. Depending on the presence of environmental influences which may affect the emission of light by the luminescent material, the wavelength selective light detectors 220a, 220b, 220c, and 220d detect light emitted by the luminescent material that is within their respective wavelength ranges. The wavelength selective light detectors 220a, 220b, 220c, and 220d output current or voltage signals having values indicating the intensity of the light detected within their respective wavelength ranges.

Figure 5:
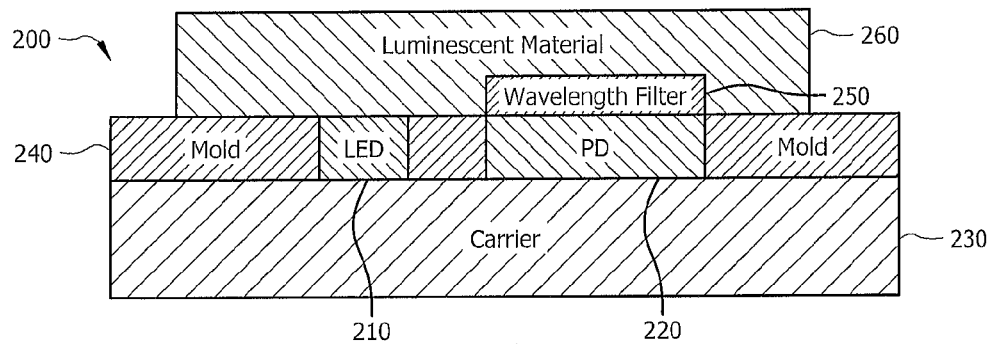
FIG. 5 illustrates a compact system including an optoelectronic module with a luminescent material directly attached to the surface of the optoelectronic module according to an illustrative embodiment.

FIG. 5 illustrates a system including an optoelectronic module 200 with a luminescent material 260 directly attached to the surface of the optoelectronic module according to an illustrative embodiment. The luminescent material 260 may be directly attached by methods such as spin coating, ink-jet-printing, stencil-printing, spraying, etc. Structuring may be done either during the application process, e.g., by masking or lift off, or, if a planar depletion is applied, after depletion, e.g., by masking and chemical solving.

Figure 6:
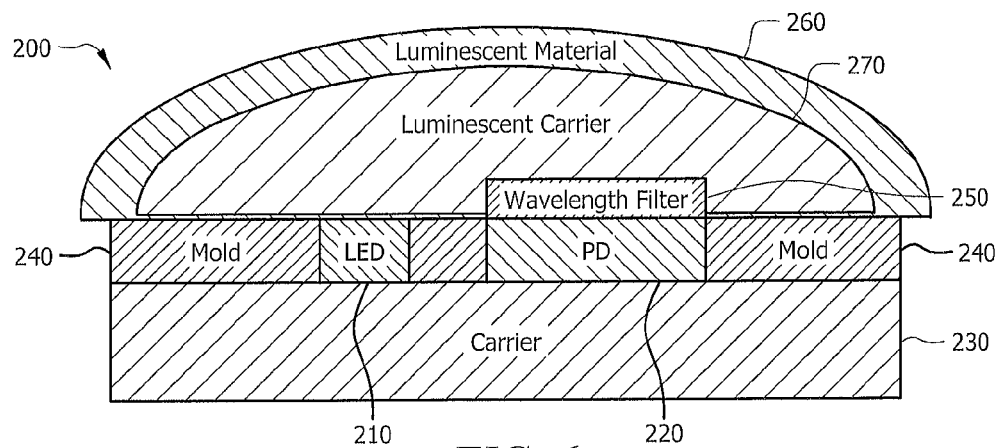
FIG. 6 illustrates a compact system including an optoelectronic module with a luminescent material mounted on a luminescent carrier according to an illustrative embodiment.

As an alternative, the luminescent material 260 may be mounted on a luminescent carrier 270 which is attached to the optoelectronic module, as illustrated in FIG. 6. The luminescent carrier 270 may be transmissive or translucent for light having the excitation wavelength and light having the emission wavelength.

According to an illustrative embodiment, the luminescent carrier 270 may be attached to the optoelectronic module 200 using an adhesive, such as glue. According to another embodiment, the luminescent carrier 270 may be attached to the optoelectronic module 200 using any suitable mounting material to create a distance between the luminescent carrier and the optoelectronic module. The luminescent material may be attached to a carrier module which is mounted to the optoelectronic module.

Figure 7:
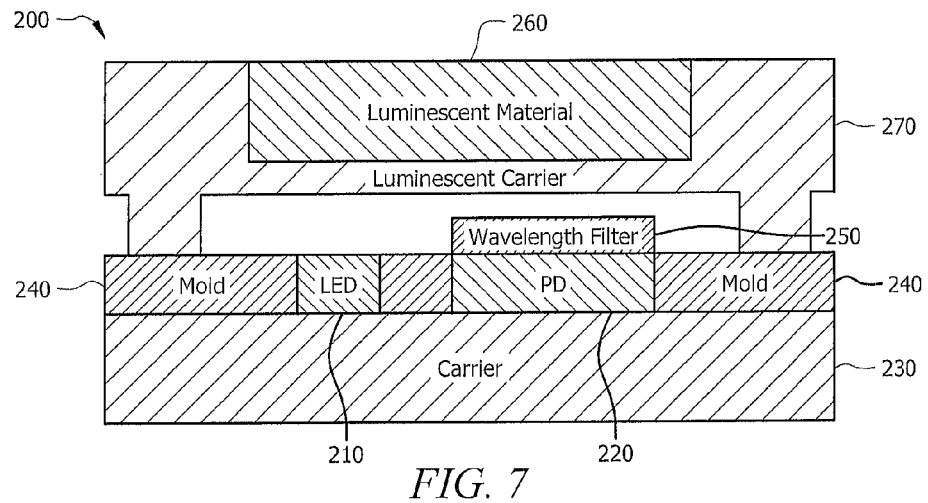
FIG. 7 illustrates a compact system including a luminescent carrier having a mechanical structure for aligning a luminescent material with an optoelectronic module according to an illustrative embodiment.

According to another embodiment, as shown in FIG. 7, the luminescent carrier 270 may be included in a mechanical structure for aligning the optoelectronic module 200 with the luminescent carrier 270. The mechanical structure may include pins (not shown) for adjustment and mounting. The mechanical structure may be disposed above the optoelectronic module 200, as shown in FIG. 7. Alternatively, the mechanical structure may be partially disposed within the mold 240 and the carrier 230. According to yet another embodiment, the mechanical structure may extend outside of the optoelectronic module 200, e.g., surrounding a portion of the module 200.

Figure 8:
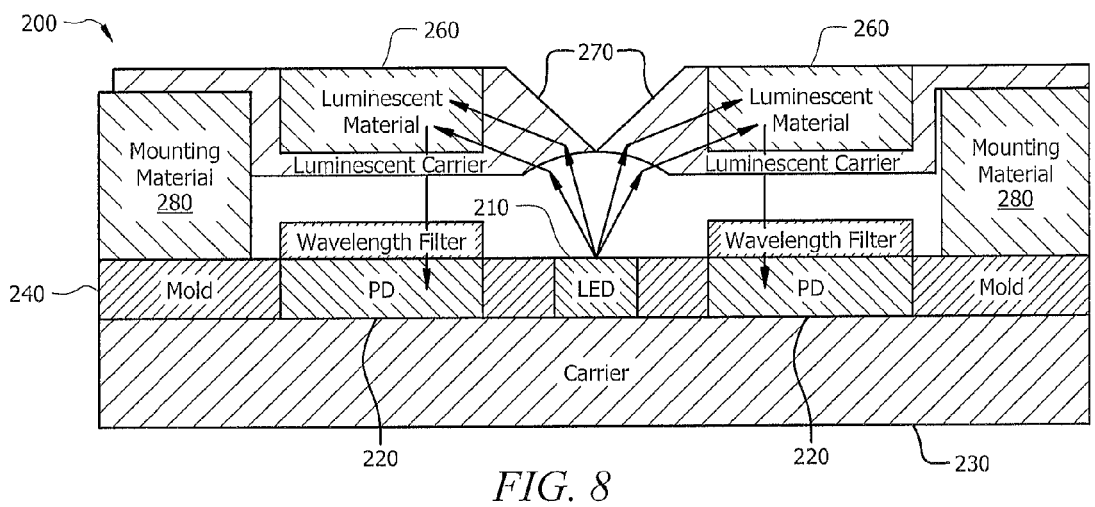
FIG. 8 illustrates a compact system including a luminescent carrier having a light guiding structure according to an illustrative embodiment.

According to another embodiment, the luminescent carrier 270 may include mechanisms to select wavelength, e.g., filters, gratings, absorption layers, etc. The luminescent carrier 270 may include mechanisms to influence the light propagation, e.g., lenses or reflectors included within a light guiding structure, as shown in FIG. 8. The light guiding structure guides light from the LED 210 to the luminescent material 260. Light from the luminescent material 260 is, in turn, directed towards the PDs 220. It should be appreciated that the PDs 220 may have the same or different predetermined wavelength ranges. Also, the luminescent materials 260 may have the same or different luminescent properties, as described in further detail below.

In yet another embodiment, the luminescent carrier 270 may be formed as a basin structure filled by the luminescent material 260 and supported by a mounting material in contact with the optoelectronic module 200. In still another embodiment, the luminescent carrier 270 may be a sponge structure containing the luminescent material 260. The sponge is a particularly useful carrier for a liquid luminescent material. The sponge structure may be in contact with the optoelectronic module 200.

In yet another embodiment, the luminescent carrier 270 may be formed of an isolating material, such as glass, to isolate the optoelectronic module 200 from the luminescent material 260. The surface of the optoelectronic module 200 may be covered with a protection layer or an isolating plate that provides galvanic and chemical isolation of the optoelectronic module. Additionally, hermetic isolation of the optoelectronic module may be achieved by, for example, replacing the mold 240 with a suitable ceramic material, using a glass lid for the luminescent carrier 270, placing the luminescent material 260 on the exterior of the glass lid, and using the a glass soldering process to solder the glass lid to the ceramic material. The result of this process is a hermetically-sealed package.

Figure 9:
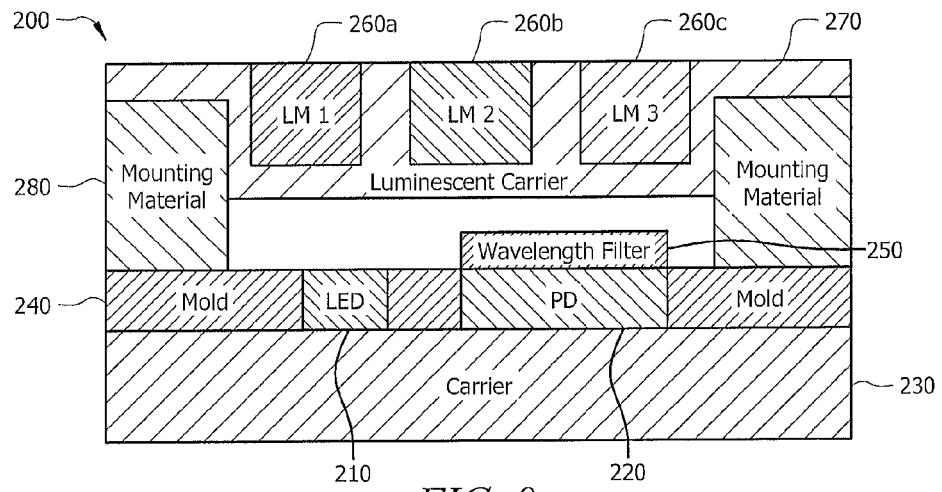
FIG. 9 illustrates a compact system including a luminescent carrier supporting multiple luminescent materials according to an illustrative embodiment.

FIG. 9 illustrates a system including a luminescent carrier supporting multiple luminescent materials according to an illustrative embodiment. In an illustrative embodiment, the luminescent materials 260a, 260b, and 260c are laterally arranged within the luminescent carrier 270, and the luminescent carrier 270 is supported by the mounting material 280. Each of the luminescent materials 260a, 260b, and 260c contains properties that cause it to react differently to the light emitted by the LED 210 and environmental influences.

For example, the luminescent material 260a may react to the presence of a particular concentration of a gas, absorbing the light emitted by the LED 210 but not emitting light of a detectable intensity at a wavelength within the predetermined wavelength range of the PD 220. The luminescent materials 260b and 260c may be unaffected by the presence of the gas, absorbing the light emitted by the LED 210 and emitting light of detectable intensities at respective wavelengths that are within the predetermined wavelength range of the PD 220. When light within the predetermined wavelength range of the PD 220 is not detected from the luminescent material 260a, this may be an indication that the gas is present in such a concentration that it causes the luminescent material 260a to not emit light of a detectable intensity. The PD 220 outputs current and voltage values corresponding to the intensity of light detected from the luminescent materials 260a, 260b, and 260c.

It should be appreciated that the invention is not limited to the arrangement of luminescent materials 260a, 260b, and 260c shown in FIG. 9. The luminescent materials may be arranged in any manner within the luminescent carrier 270. For example, the luminescent materials 260a, 260b, and 260c may be vertically stacked within the luminescent carrier 270. As an alternative, the luminescent materials 260a, 260b, and 260c may be combined homogeneously, e.g., in the case of three liquid luminescent materials being mixed together.

Although not illustrated, it should be further appreciated that a compact system may comprise multiple light sources, multiple wavelength selective light detectors, and multiple luminescent materials.

Figure 10:
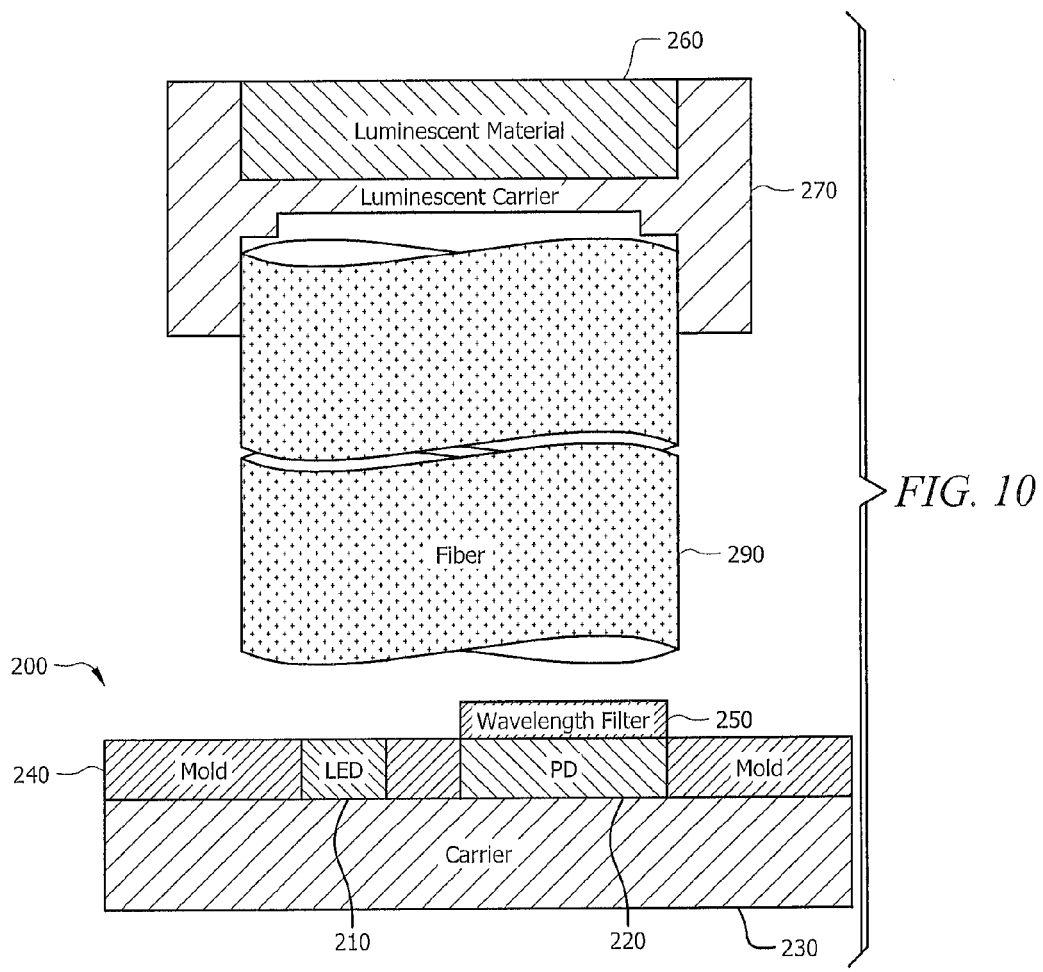
FIG. 10 illustrates a compact system including an optoelectronic module connected to an optical fiber with a luminescent carrier attached to the end of the optical fiber according to an illustrative embodiment.

FIG. 10 illustrates a system including an optoelectronic module connected to a luminescent carrier by an optical fiber according to an illustrative embodiment. In the embodiment shown in FIG. 10, the luminescent carrier 270 is connected to the end of an optical fiber 290. The optical fiber 290 is, in turn, coupled to the optoelectronic module 200. According to other alternatives, the luminescent material 260 may be directly applied to the end of the optical fiber 290, the optical fiber 290 may be coated on the outside with the luminescent material 260, or the luminescent material may be applied within the optical fiber cladding or optical fiber core. As yet another alternative, the luminescent carrier 270 may be applied at one more discrete locations along the optical fiber 290, as shown in FIG. 11.

In all of arrangements of luminescent materials on or within an optical fiber 290 described above, the optical fiber 290 operates to transmit light emitted at a predetermined excitation wavelength by one or more LEDs 210 to the luminescent material 260, and the luminescent material 260 absorbs the light. Depending on environmental influences, the luminescent material 260 emits light at a variable emission wavelength, and the emitted light is transmitted by the optical fiber 290 to one or more PDs 220. Light of a detectable intensity within the predetermined wavelength of the PD 220 is detected by the PD 220. The PD 220 outputs a current or voltage signal having a value indicative of the intensity of detected light.

Figure 11:
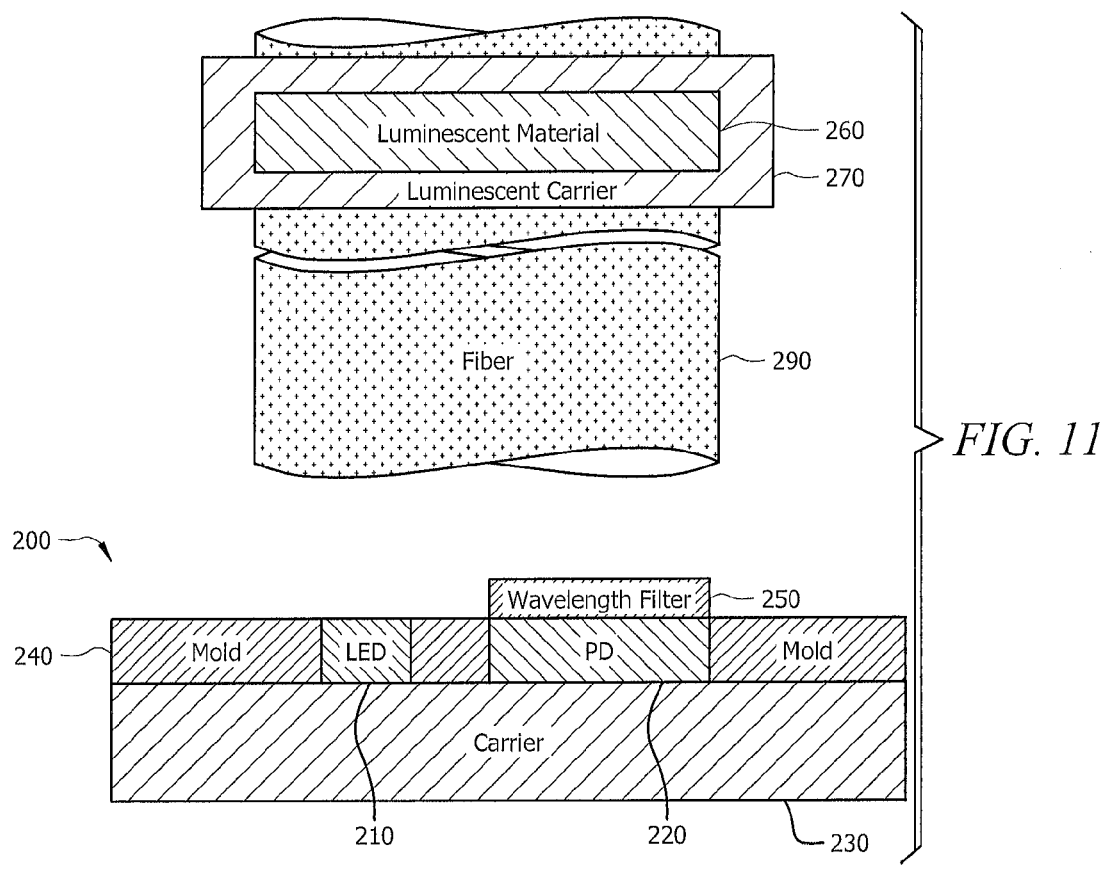
FIG. 11 illustrates a compact system including an optoelectronic module connected to an optical fiber with a luminescent carrier disposed along a portion of the optical fiber according to an alternative illustrative embodiment.

As illustrated in FIGS. 10 and 11, the optical fiber 290 may be coupled to the optoelectronic module 200 by butt coupling an end of the optical fiber 290 to the optoelectronic module 200. Although not illustrated, it should be appreciated that the optical fiber 290 such as that described above may be coupled to the optoelectronic module 200 in a number of different ways. As an illustrative example, the optoelectronic module 200 may be coupled to the optical fiber 290 via coupling optics, such as a lens. The lens may be shaped as desired to direct light through the optical fiber 290.

Figure 12A:
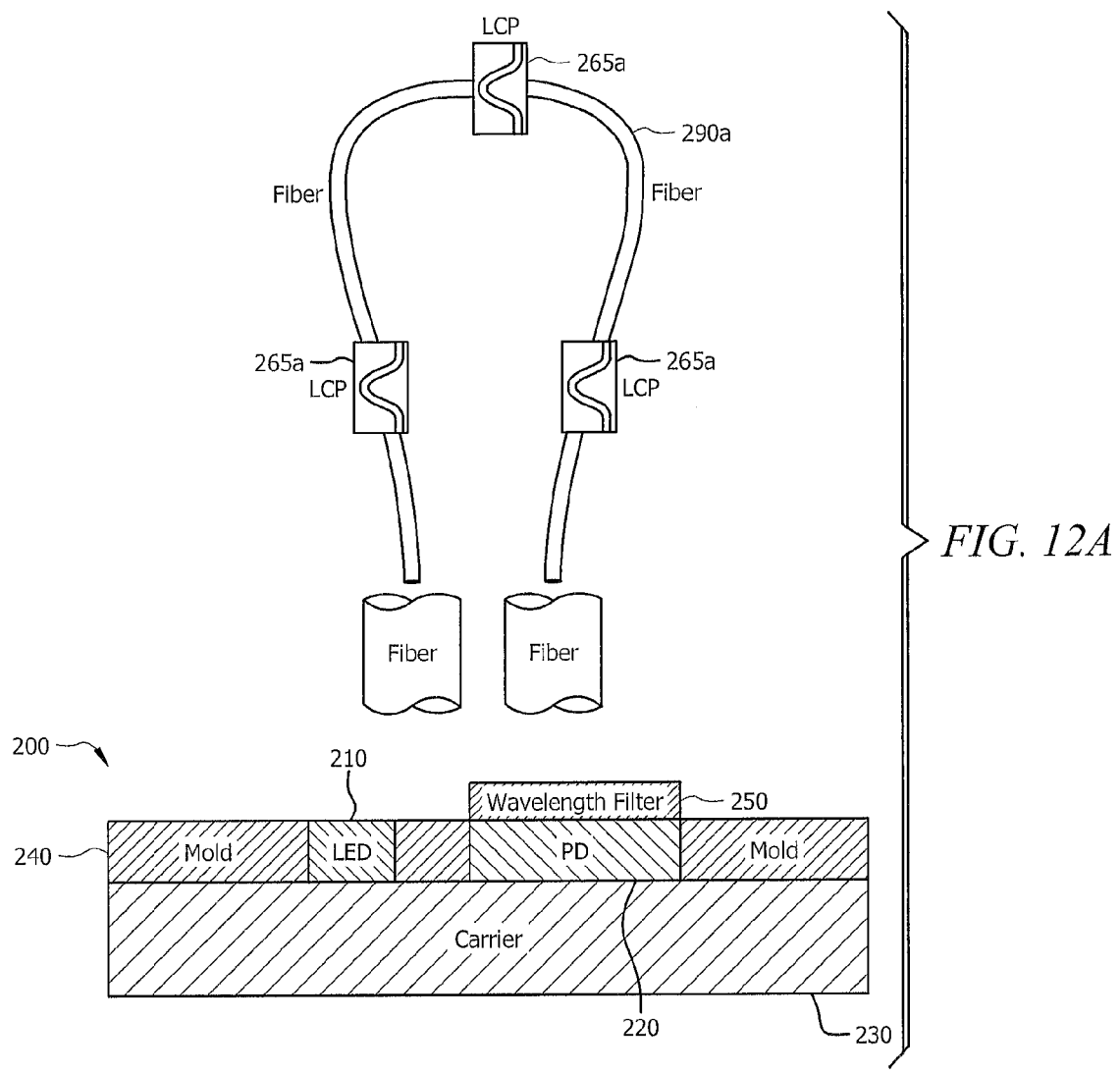
FIGS. 12A-12C illustrate examples of configurations of optical fibers attached to optoelectronic modules according to illustrative embodiments.
Figure 12B:
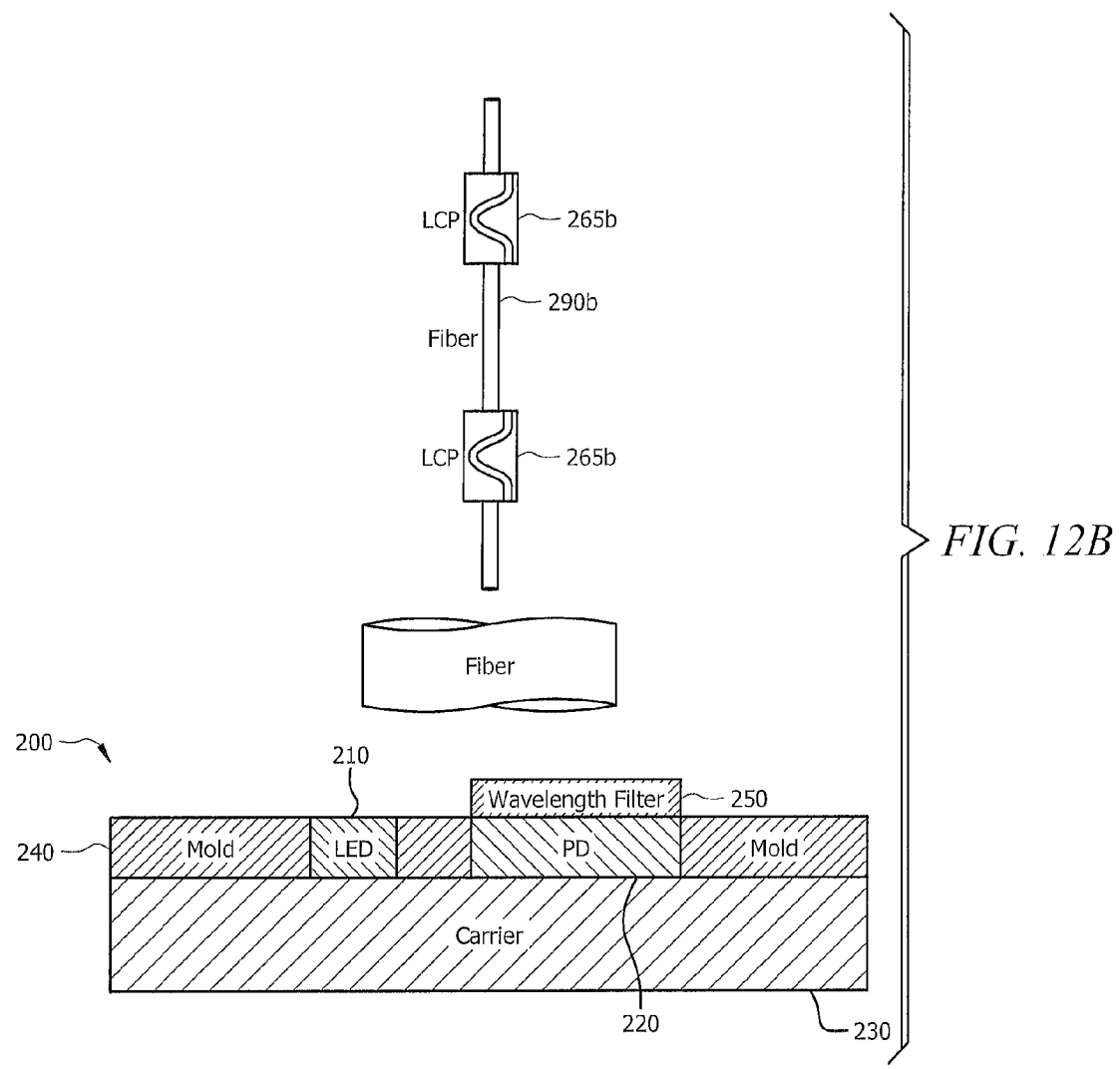
Figure 12C:
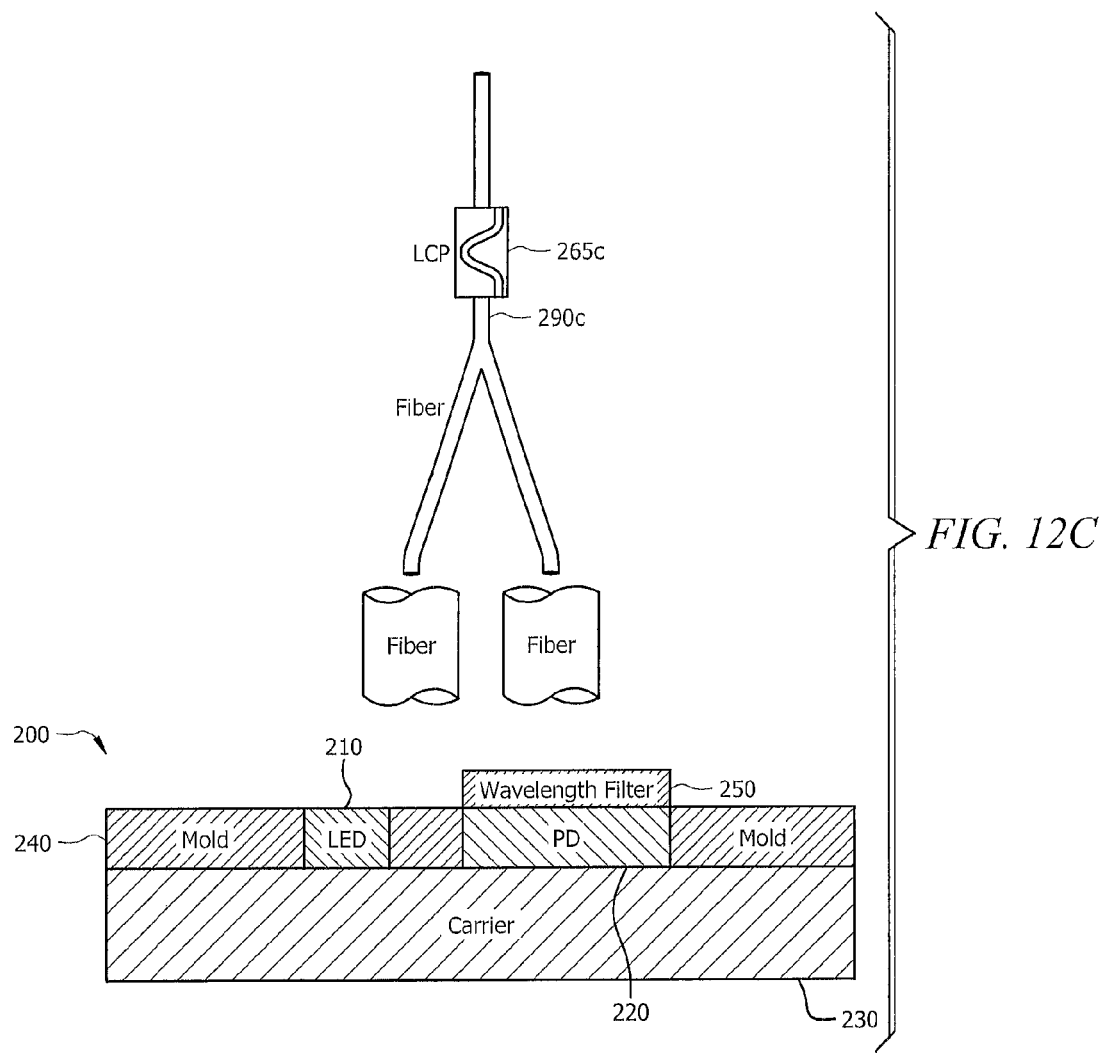

FIGS. 12A-12C illustrate examples of optical fiber configurations with luminescent carriers applied at discrete places along an optical fiber according to illustrative embodiments. It should be appreciated that the scale of the optical fiber in FIGS. 12A-12C differs, such that the bodies of the optical fiber appear smaller to illustrate the different configurations, while the ends of the optical fiber coupled to the optoelectronic module appear larger. It should further be appreciated that these configurations are not limited to implementations with the luminescent carriers 270 applied at discrete places along the optical fiber. These configurations may also be implemented with the luminescent material 260 applied directly to the end of the optical fiber, applied directly to the outside of the optical fiber, or applied directly within the optical fiber.

Referring to FIG. 12A, a loop optical fiber configuration is shown, in which the luminescent carrier supporting the luminescent material is applied at discrete places along an optical fiber 290a loop at luminescent coupling points (LCPs) 265a. The ends of the optical fiber 290a are coupled to the optoelectronic module 200 (with one end of the fiber 290a connected to the LED 210, and the other end of the fiber 290 connected to the PD 220). Light emitted by the LED 210 is transmitted by the optical fiber to the luminescent material(s) located at the LCPs 265a, and light emitted by the luminescent material(s) is transmitted to the PD 220 by the optical fiber 290a.

In FIG. 12B, a line optical fiber configuration is shown, in which the luminescent carrier supporting the luminescent material is applied to a line optical fiber 290b at LCPs 265b, and an end of the optical fiber 290b is connected to the optical electronic module 200 (with the LED 210 and the PD 220 connected to the same end of the fiber 290b). Light from the LED 210 is transmitted by the optical fiber 290b to the luminescent material(s) at the LCPs 265b, and light emitted by the luminescent materials(s) is, in turn, transmitted to the PD 220 via the optical fiber 290b.

In FIG. 12C, a line optical fiber configuration with a combiner, such as a 3 dB coupler, is shown, in which a luminescent carrier supporting the luminescent material is applied to an optical fiber 290c at an LCP 265c. The optical fiber 290c branches out into distinct lines that are, in turn, each coupled to the optoelectronic module 200 (with one line connected to the LED 210 and the other line connected to the PD 220). In the configuration shown in FIG. 12c, the left portion of the optical fiber 290 transmits light from the LED 210 to the luminescent material at the LCP 265c, and the right portion of the optical fiber 290 carries light emitted by the luminescent material at the LCP 265c to the PD 220.

It should be appreciated that the optical fiber configuration shown in FIGS. 12A-12C are examples of optical fiber configurations, and that other optical fiber configurations may be used. For example, although in the configurations illustrated in FIGS. 12A and 12C, the LED 210 and the PD 220 are connected to different ends of an optical fiber, it should be appreciated that the LED 210 and the PD 220 may be connected to the same end of an optical fiber. This may be achieved by, for example, using a power-over-fiber cable.

Figure 13:
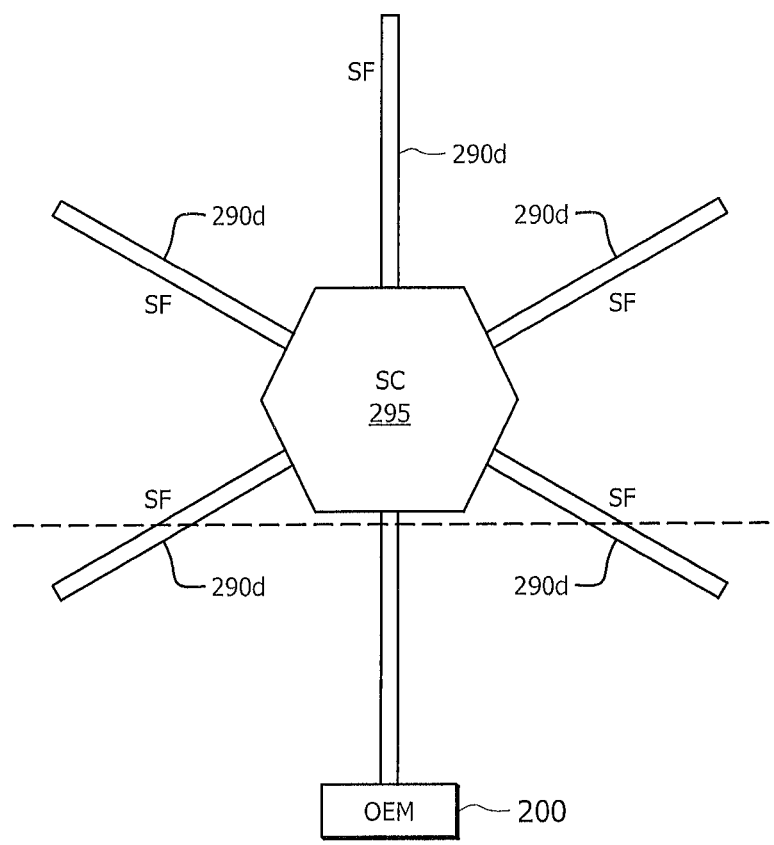
FIG. 13 illustrates an example of a star optical fiber configuration according to an illustrative embodiment.

FIG. 13 illustrates a star optical fiber configuration according to an illustrative embodiment. The star optical fiber configuration includes sensor optical fibers (SF) 290d having luminescent carriers and/or luminescent materials applied thereon, in any of the manners described above. The luminescent material applied to or coupled to each SF 290d may be the same or different. The SFs 290d are coupled to the optoelectronic module (OEM) 200 via a star coupler (SC) 295, e.g., a Rosetta coupler. The OEM 200 may include one or more light sources and one or more wavelength selective light detectors.

The OEM 200 emits light at one or more predetermined excitation wavelength(s), and the light is absorbed by the luminescent material applied to (or within luminescence carriers applied to) the SFs 290d. Dispending upon environmental influences on the luminescent material(s), light is emitted by the luminescent material(s) at one or more variable wavelengths, and the emitted light that is of a detectable intensity that is within the predetermined wavelength range of the wavelength selective light detector(s) within the OEM 200 is detected. A current/voltage signal may be output by the wavelength selective light detector(s) within the OEM 200 with a value that corresponds to the intensity of the detected light. If light is not detected within the predetermined wavelength range from one or more of the SF's 290d, the value of the current/voltage signal may reach a threshold that causes an alarm to be generated, in a manner similar to that described above.

Although one OEM 200 is shown in FIG. 13, it should be appreciated that multiple OEMs may be used. For example, one OEM 200 may be used to transmit light at one wavelength and detect light within a first wavelength range, and another OEM may be used to transmit light at another wavelength and detect light within a second wavelength range.

Figure 14A:
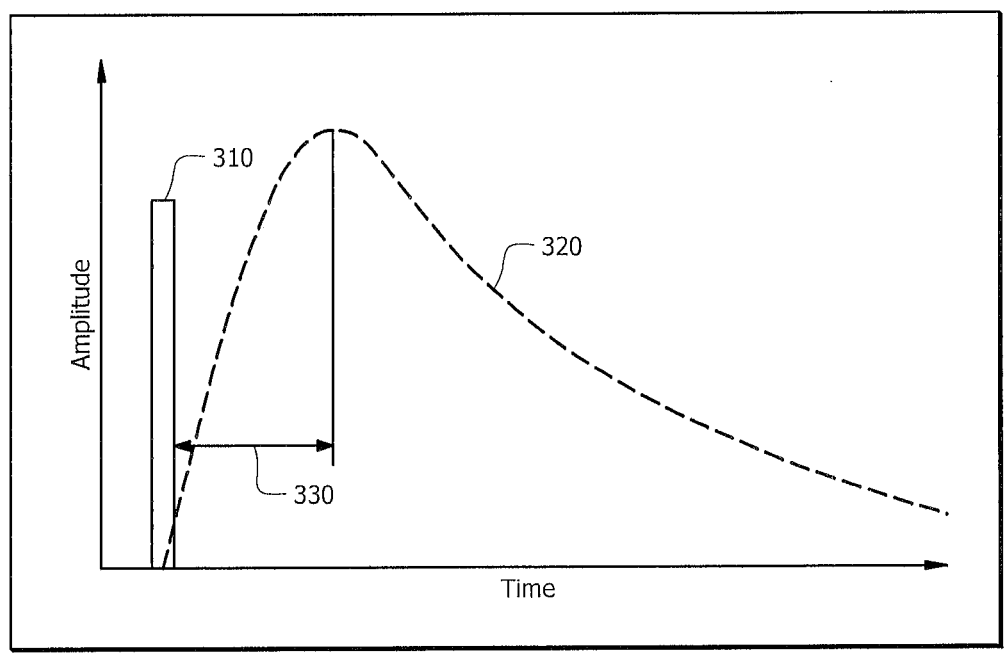
FIGS. 14A and 14B graphically illustrate emission of light by a luminescent material responsive to pulse excitation and periodic excitation from a light source, respectively, according to illustrative embodiments.
Figure 14B:
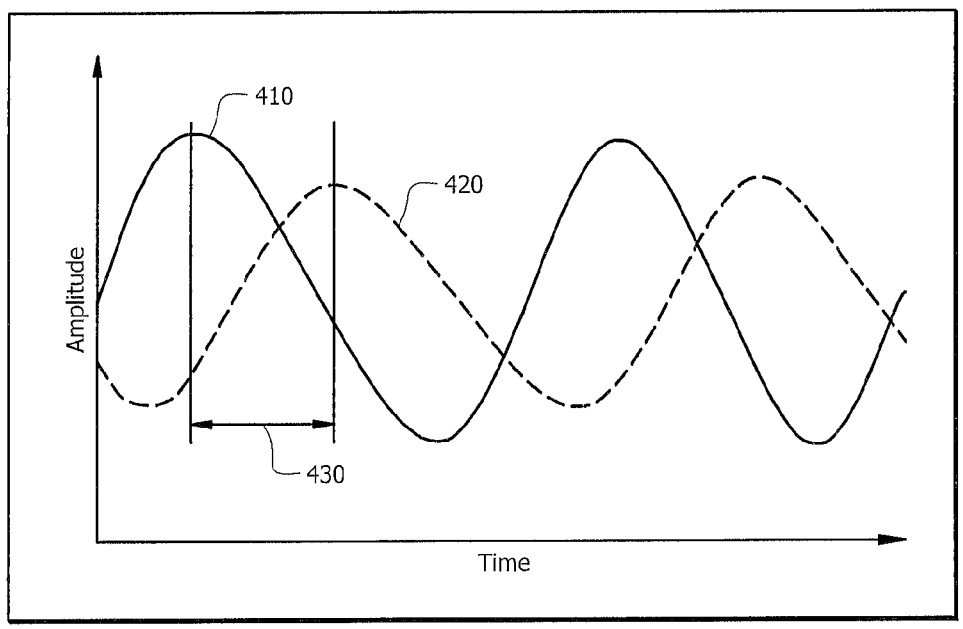

FIGS. 14A-14B graphically illustrate emission of light from a luminescent material responsive to pulse excitation and periodic excitation, respectively, according to illustrative embodiments. Referring to FIG. 14A, according to one embodiment, a pulse of light 310 of a particular amplitude is emitted by the optoelectronic module 200. The luminescent material 260 absorbs the light and emits light 320 of a different amplitude. As can be seen from FIG. 14A, there is a time delay, referred to as a recombination time 330, between the emission of the pulse of light 310 by the optoelectronic module and the emission of light 320 by the luminescent material. Additionally, the light 320 emitted by the luminescent material fades exponentially over time.

According to another embodiment, the optoelectronic module 200 periodically emits light 410 of a particular amplitude, as shown in FIG. 14B. The luminescent material 260 absorbs the emitted light and, in response, periodically emits light 420 of a different amplitude. The time difference between the emission of light 410 and the emission of light 420 may be referred to as the phase shift 430. The phase shift 430 is independent of the frequency of emission of light by the optoelectronic module 200. Absent environmental influences which may affect the emission of light by the luminescent material 260, the phase shift 430 is constant over time, given a constant periodic emission of light by the optoelectronic module 200. However, if the emission of light by the luminescent material changes due to environmental influences, e.g., the presence of a harmful gas causes the luminescence material to stop or delay the emission of light over a period of time, this changes the phase shift 430. Thus, a difference in the phase shift 430 may be used as another indicator of environmental influences on the luminescent material.

According to an illustrative embodiment, the difference in phase shift 430 over time may be measured using a phase comparator integrated within the optoelectronic module 200 or connected electronically to the LED 210 and the PD 220 (not shown for simplicity of illustration). The phase comparator compares an electrical signal applied to the LED 210 and/or detected by the PD 220 without the influence of emission by the luminescent material 260 to a signal emitted by the luminescent material 260 and the PD 220 over time. Absent the presence of environmental influences which may affect the emission of light by the luminescent material, the comparison of the signals will result in a constant value. However, if environmental influences affect the emission of light by the luminescent material, the comparison of signals will result in a different value, indicating a phase shift.

Phase comparison may be performed by the wavelength selective light detector formed via monolithic integration, using an application specific integrated circuit (ASIC) or an off-the-shelf product. Any other suitable off-the-shelf phase comparator may be used for phase comparison, using signals from the wavelength selective light detector, such as the MM54C932/MM743932 phase comparator manufactured by Texas Instruments™.

Figure 15:
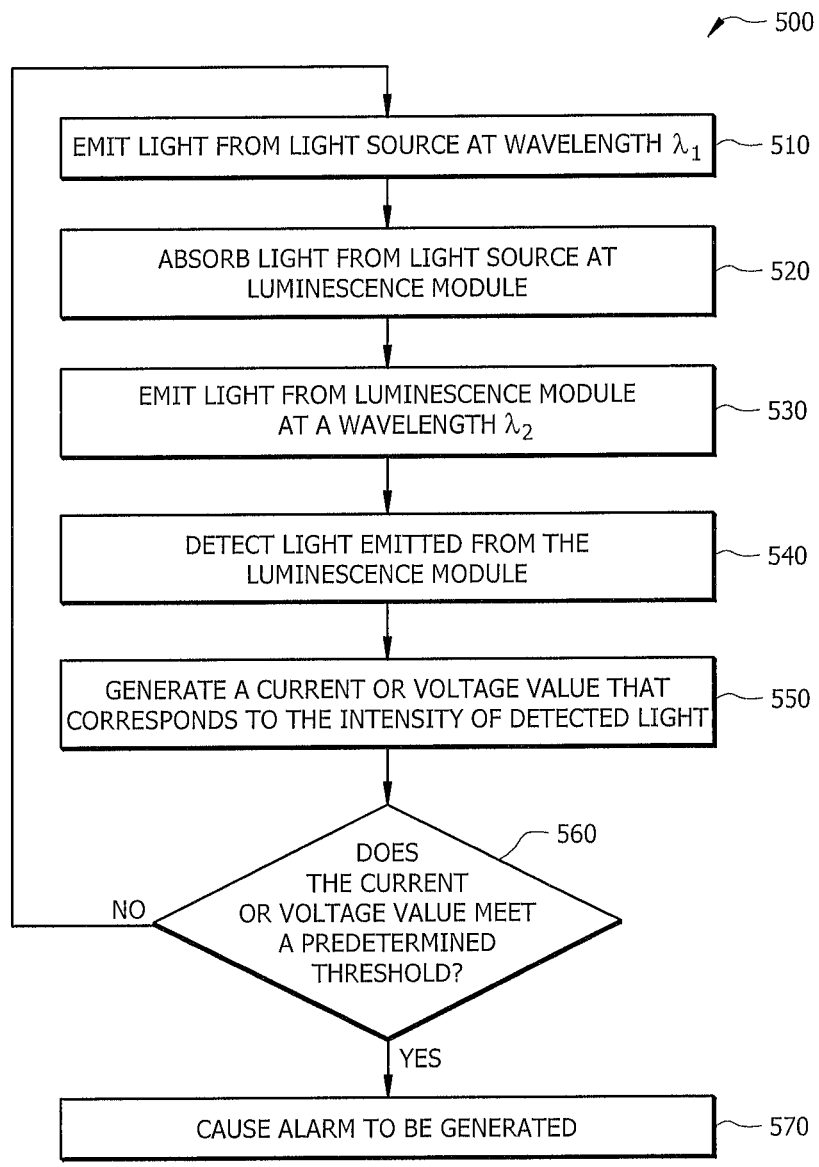
FIG. 15 illustrates a method for sensing luminescent activity according to an illustrative embodiment.

FIG. 15 illustrates a method 500 for sensing luminescent activity according to an illustrative embodiment. It should be understood that the steps have been presented in the demonstrated order for ease of description and illustration but that the order of the steps need not be limited to the description below. Steps can be added, omitted and/or performed simultaneously without departing from the scope of the appended claims. It should also be understood that the method can be ended at any time.

Referring to FIG. 15, at step 510, light from a light source, e.g., the light source 120, is emitted at a predetermined excitation wavelength $\lambda_1$. At step 520, light from the light source 120 is absorbed by a luminescent material, e.g., the luminescent material 150 within the luminescent module 140. At step 530, depending upon environmental influences in the area surrounding the compact system 100, light is emitted by the luminescence module 140 at a variable emission wavelength $\lambda_2$. It should be appreciated that, depending upon the environmental influences on the luminescent material 150, this step may not occur to an extent that is significant. That is, environmental influences may affect the emission of the light by the luminescent material 150 such that the luminescence module does not emit light, or the intensity of the light emitted by the luminescence module is so negligible that is it undetectable by the wavelength selective light detector 130.

At step 540, light emitted by the luminescence module 140 is detected by the wavelength selective light detector 130, and at step 550, a current or voltage value is produced that corresponds to an intensity of the detected light. The intensity of the detected light corresponds to an extent to which an environmental influence, such as a particular gas, affects the emission of light by the luminescent material 150. For example, in the scenario in which the luminescent material is impacted by a particular gas which affects the emission of light by the luminescent material, the current or voltage value indicates the concentration of the gas in the area surrounding the luminescent material.

According to an illustrative embodiment, if the current or voltage value reaches a certain threshold, the wavelength selective light detector 130 may output a current or voltage value that causes an alarm to be generated. Thus, at step 560, a determination is made whether the current or voltage value produced by the wavelength selective light detector 130 reaches the predetermined threshold. This determination may be made by logic included in the wavelength selective light detector 130 or by a processor that receives the current or voltage value from the wavelength selective legit detector. The current or voltage threshold may correspond to a value emitted when no light is detected by the wavelength selective light detector 130. If the current or voltage value meets the predetermined threshold, this may be indicative of an environmental influence on the luminescent material which causes the luminescent material not to emit light of a detectable intensity. Thus, according to an illustrative embodiment, when the current or voltage value generated by the wavelength selective light detector 130 reaches a predetermined threshold, this may cause an alarm to be generated at step 570, as described above.

As indicated above, the optoelectronic systems and devices described above can be made very compact in size. A process technology known as embedded Wafer-Level Packaging (eWLP) technology may be used to make the optoelectronic devices and systems described herein. Application Ser. Nos. 14/330,022 and 14/213,342, which are incorporated by reference herein, disclose the use of eWLP technology to fabricate very compact optoelectronic devices, systems and assemblies. In the interest of brevity, the manner in which such technology can be used to fabricate optoelectronic systems and devices of the type described herein will not be described because persons of skill in the art will understand, in view of the descriptions provided in those applications and in this application, the manner in which eWLP technology can be used to fabricate optoelectronic systems and devices of the type described herein.

In general, the descriptions provided in application Ser. Nos. 14/330,022 and 14/213,342 describe using eWLP technology to fabricate various types of eWLP optoelectronic devices or packages that include one or more transmitter chips such as a laser diode or LED chips that emit light of a particular wavelength and one or more receiver chips such as photodiode chips that detect light of particular wavelengths. The process steps of placing the LED(s), the laser diodes, the photodiodes, the luminescence material, the luminescence carrier and any wavelength filter(s) can be performed at the eWLP wafer level. Alternatively, some of those process steps can be performed at the wafer level whereas others can be performed at the package level, i.e., after the wafer has been sawed.

Figure 16:
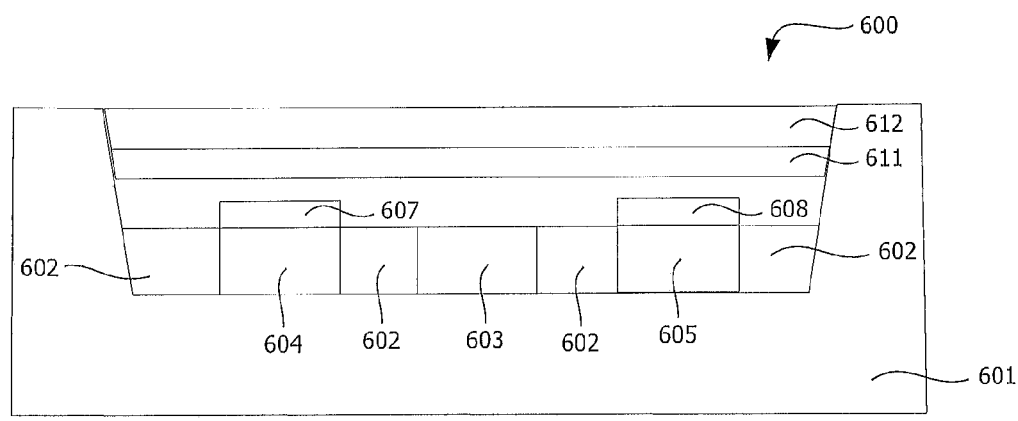
FIG. 16 illustrates a side cross-sectional view of an eWLP optoelectronic package in accordance with an illustrative embodiment that has been fabricated using the eWLP technology.
Figure 17:
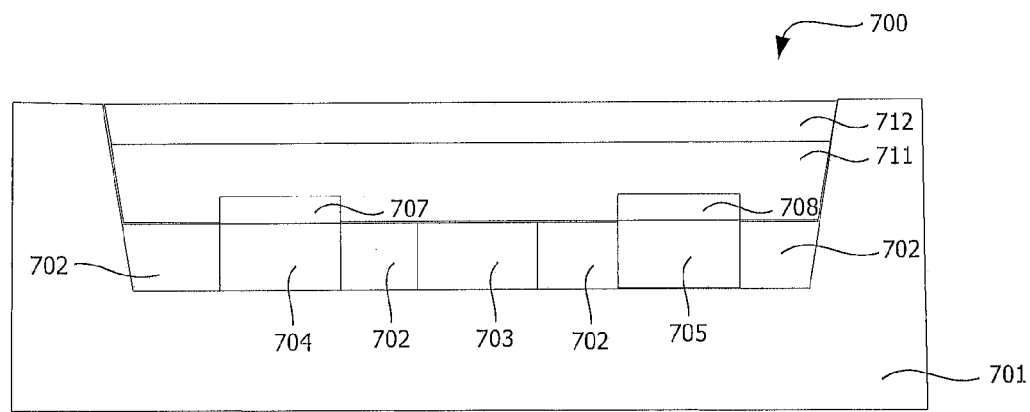
FIG. 17 illustrates a side cross-sectional view of an eWLP optoelectronic package in accordance with another illustrative embodiment that has been fabricated using the eWLP technology.

FIGS. 16 and 17 are side cross-sectional views of eWLP optoelectronic packages that have been fabricated using the aforementioned eWLP technology. The eWLP optoelectronic package 600 shown in FIG. 16 includes a package carrier 601, a mold material 602, an LED 603 secured in and surrounded on its sides by the mold material 602, first and second PDs 604 and 605 secured in and surrounded on their sides by the mold material 602, first and second wavelength filters 607 and 608 disposed on top of the first and second PDs 604 and 605, respectively, a luminescent material carrier 611 disposed above the mold material 602, the first and second wavelength filters 607 and 608 and the LED 603, and a luminescent material 612 disposed on top of the luminescent material carrier 611.

The eWLP optoelectronic package 600 can perform any of the functions described above with respect to FIGS. 1-14 to sense luminescence and/or changes in luminescence indicative of environmental influences, such as the presence and/or concentration of a gas or chemical, ambient temperature, pressure, light, etc., in an area surrounding a luminescent material 612. The mold material 602 is a cured, hard plastic material applied in liquid form and cured at the wafer level. The cured mold material 602 provides mechanical stability for the eWLP optoelectronic package 600. In accordance with this embodiment, the luminescent material carrier 611 serves as a lid that seals off the portion of the package below the carrier 611 from the environment.

The eWLP optoelectronic package 700 shown in FIG. 17 includes a package carrier 701, a mold material 702, an LED 703 secured in and surrounded on its sides by the mold material 702, first and second PDs 704 and 705 secured in and surrounded on their sides by the mold material 702, first and second wavelength filters 707 and 708 disposed on top of the first and second PDs 704 and 705, respectively, a luminescent material carrier 711 covering the mold material 702, the first and second wavelength filters 707 and 708 and the LED 703, and a luminescent material 712 disposed on top of the luminescent carrier 711. In this embodiment, the luminescent material carrier 711 is a transparent potting compound that provides mechanical stability for the package 700 of a type that is commonly used in LED technology. The luminescent material carrier 711 seals off the portion of the package below the carrier 711 from the environment.

The eWLP optoelectronic packages 600 and 700 can perform any of the functions described above with respect to FIGS. 1-14 to sense luminescence and/or to sense changes in luminescence indicative of environmental influences, such as the presence and/or concentration of a gas or chemical, ambient temperature, pressure, light, etc., in an area surrounding a luminescent material.

Using the eWLP methods described in application Ser. Nos. 14/330,022 and 14/213,342 to make the packages 600 and 700 allows many advantages to be realized including, for example, eliminating the need for bond wires for making back side electrical interconnections, eliminating the need for housings for the optoelectronic devices, packages and assemblies, and allowing a variety of very thin, compact optoelectronic devices, packages and assemblies having a various useful configurations to be made with high volume, high yield and high throughput. The eWLP methods allow packages such as packages 600 and 700 to be made with overall sizes on the order of 1 mm$^2$.

As indicated above, the optoelectronic system, package or device in accordance with the embodiments described herein will typically be equal to or less than about 9 mm$^2$ in size, but can be made much smaller using the aforementioned eWLP methods. However, compact optoelectronic devices, systems or packages of the type described above and shown in the figures can also be made using other technologies, such as Plastic Lead Chip Carrier (PLCC) technology (e.g., PLCC4 and PLCC6), for example. PLCC is suitable for making the optoelectronic devices, systems or packages described herein. In PLCC technology, premolded plastic leadframes are used for mounting the components.

Figure 18:
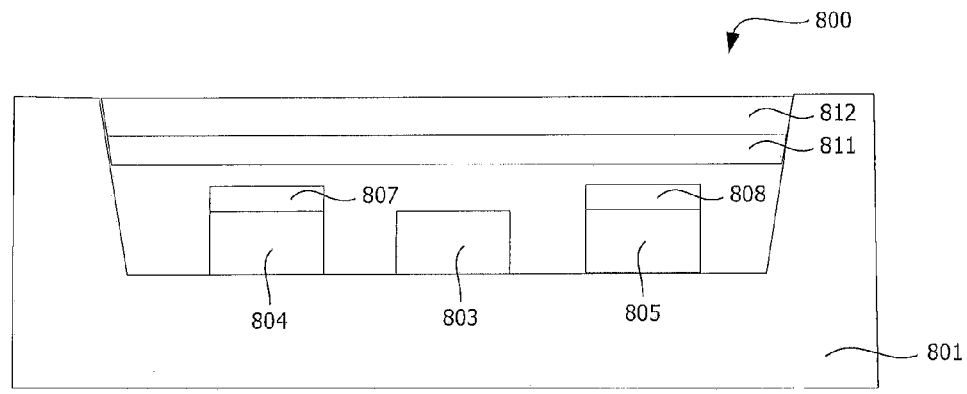
FIG. 18 illustrates a side cross-sectional view of a Plastic Lead Chip Carrier (PLCC) optoelectronic package in accordance with an illustrative embodiment that has been fabricated using the PLCC technology.
Figure 19:
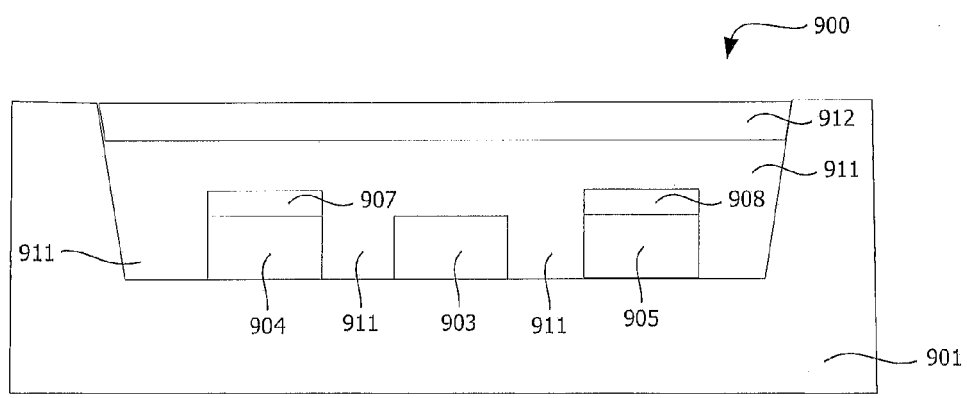
FIG. 19 illustrates a side cross-sectional view of a PLCC optoelectronic package in accordance with another illustrative embodiment that has been fabricated using PLCC technology.

FIGS. 18 and 19 illustrate side cross-sectional views of optoelectronic packages that have been fabricated using PLCC technology. While PLCC technology does not currently provide form factors as small as those which can be achieved using eWLP technology, PLCC technology is suitable for use with the invention for applications where larger form factors are acceptable. The PLCC optoelectronic package 800 shown in FIG. 18 includes a package carrier 801, which is a premolded plastic leadframe, an LED 803 secured to the carrier 801, first and second PDs 804 and 805 secured to the carrier 801, first and second wavelength filters 807 and 808 disposed on top of the first and second PDs 804 and 805, respectively, a luminescent material carrier 811 disposed above the LED 803, the first and second PDs 804 and 805, and the first and second wavelength filters 807 and 808, and a luminescent material 812 disposed on top of the luminescent material carrier 811.

In the illustrative embodiment shown in FIG. 18, the PLCC package carrier 801 provides mechanical stability for the package 800, thereby obviating the need for the mold material 602, 702 shown in FIGS. 16 and 17. However, if additional mechanical stability is needed or desired, or if needed to provide optical isolation, the mold material 602, 702 may be used in the package 800. The luminescent material carrier 811 serves as a lid that seals off the portion of the package below the carrier 811 from the environment.

The PLCC optoelectronic package 900 shown in FIG. 19 is similar to the PLCC optoelectronic package 800 shown in FIG. 18, except that package 900 includes a luminescent material carrier 911 that encapsulates the LED 903, the first and second PDs 904 and 905, and the first and second wavelength filters 907 and 908 disposed on top of the first and second PDs 904 and 905, respectively. The package carrier 901 is a premolded plastic leadframe to which the LED 903 and the first and second PDs 904 and 905 are secured, typically by soldering. The luminescent material carrier 911 is typically a transparent potting compound of a type commonly used in LED mass production. A luminescent material 912 disposed on top of the luminescent material carrier 911. The luminescent material carrier 911 seals off the portion of the package below the carrier 911 from the environment.

The PLCC optoelectronic packages 800 and 900 can perform any of the functions described above with respect to FIGS. 1-14 to sense luminescence and/or changes in luminescence indicative of environmental influences, such as the presence and/or concentration of a gas or chemical, ambient temperature, pressure, light, etc., in an area surrounding a luminescent material 812, 912.

Figure 20:
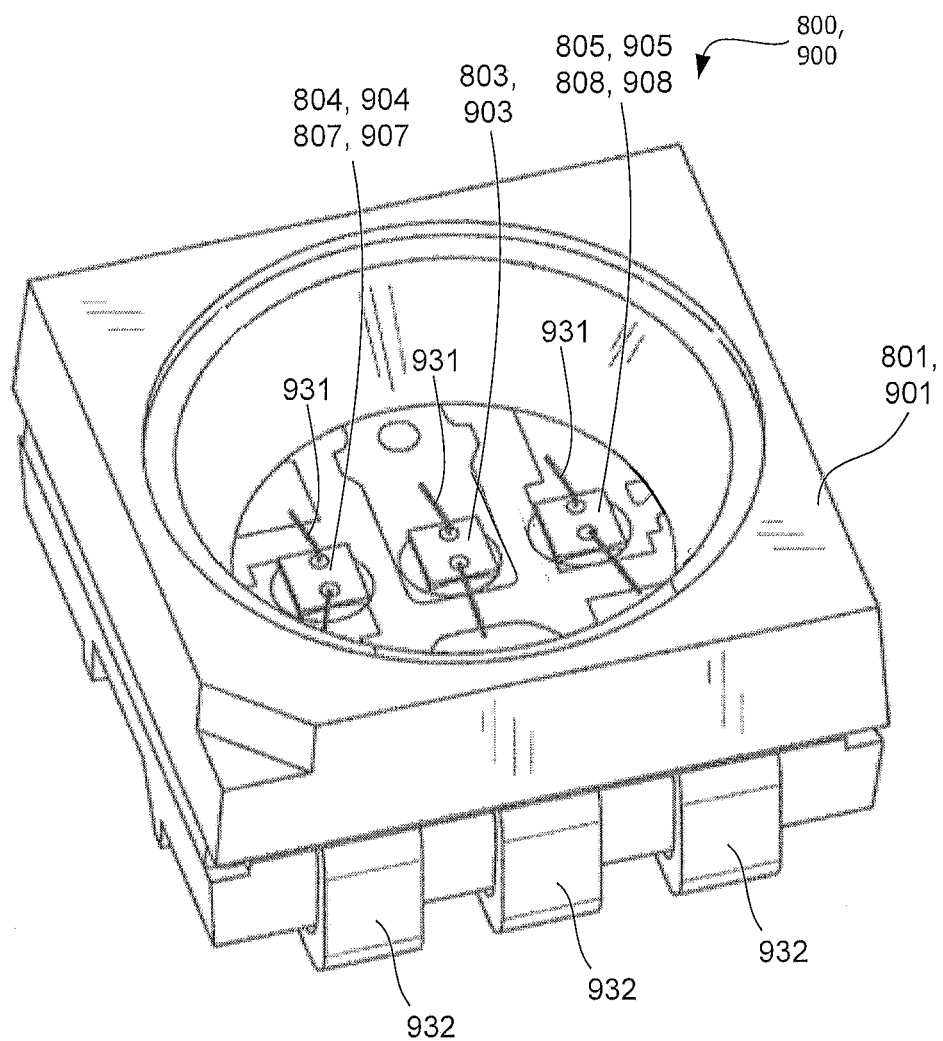
FIG. 20 illustrates a top perspective view of the PLCC optoelectronic package shown in FIGS. 18 and 19.

FIG. 20 illustrates a top perspective view of the PLCC optoelectronic package 800, 900 shown in FIGS. 18 and 19, which look identical from the top perspective view. FIG. 20 shows some features of the packages 800, 900 that are not shown in the cross-sectional views of FIGS. 18 and 19 for simplicity, such as bond wires 931 and external package leads 932. In FIG. 20, the luminescent material carrier 811, 911 and the luminescent material 812, 912 are removed to show the interior of the package 800, 900. The PD 804, 904 cannot be seen because it is covered by the filter 807, 907. Likewise, the PD 805, 905 cannot be seen because it is covered by the filter 808, 908.

Of course, the shape of the optoelectronic package 800, 900 shown in FIG. 20 is merely one example of how the optoelectronic package might be shaped. The invention is not limited with respect to the shape of the package, device or system.

Figure 21:
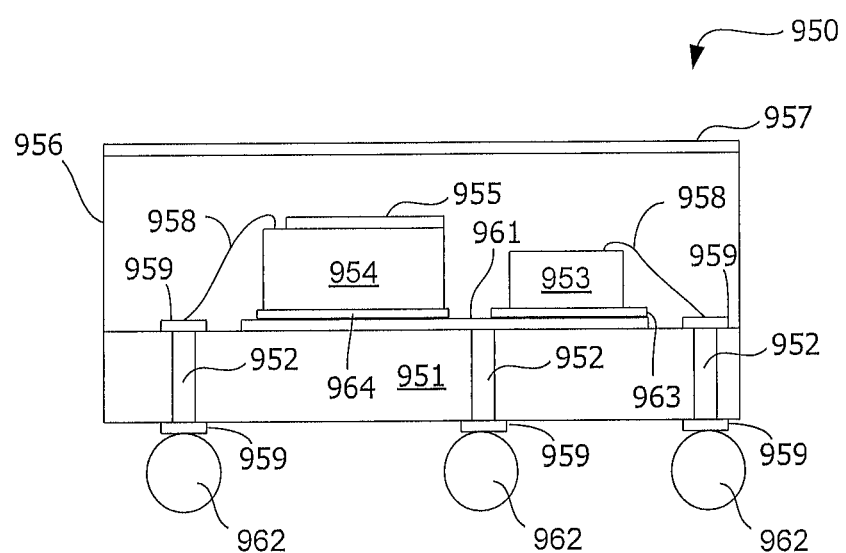
FIG. 21 illustrates a side cross-sectional view of an optoelectronic package in accordance with another illustrative embodiment.

FIG. 21 illustrates a side cross-sectional view of an optoelectronic package 950 in accordance with another illustrative embodiment. The optoelectronic package 950 may be an eWLP optoelectronic package made using the aforementioned eWLP methodologies disclosed in the aforementioned application Ser. Nos. 14/330,022 and 14/213,342. Alternatively, the optoelectronic package 950 may be made using conventional techniques. The optoelectronic package 950 includes an interposer 951 having vias 952 formed therein, an LED 953, a PD 954, a filter 955, a polymer mold 956, a luminescent material layer 957, bond wires 958, electrical contacts 959, an electrically-conductive layer 961, solder balls 962, and electrically-conductive adhesive layers 963 and 964.

The interposer 951 may be, for example, a silicon substrate in which case the vias 952 are through-silicon vias (TSVs), a glass carrier with the vias 952 formed therein, or a printed circuit board (PCB) with the vias 952 formed therein. The polymer mold 956 may be, for example, a casted layer, a spin-coated layer or an over mold. The advantage to making the mold 956 of a polymer is that it facilitates the application and adhesion of the luminescent material layer 957 better than inorganic materials such as glass, for example.

The LED 953 and PD 954 have electrical contacts (not shown) on their bottom surfaces that are electrically connected to electrodes of an external power supply (not shown) through the electrically-conductive pathway made up of the solder ball 962 in the center, the corresponding electrical contact 959 and via 952, electrically-conductive metal layer 961, and electrically-conductive adhesive layers 963 and 964. The electrically-conductive adhesive layers 963 and 964 are applied before the die-attach process The LED 953 and PD 954 have electrical contacts (not shown) on their top surfaces that are electrically connected to electrodes of the external power supply (not shown) through the electrically-conductive pathway made up of the solder balls 962 on the opposite sides of the package 950, the corresponding electrical contacts 959 and vias 952, and the bond wires 958.

The LED 953 emits light at a predetermined excitation wavelength $\lambda_1$ (or waveband $\Delta\lambda_1$). For illustrative purposes, the LED 953 is being used as the light source, but any suitable light sources may be used, including, for example, a laser diode, a SLED, etc. The luminescent material 957 absorbs the light emitted from the LED 953 that is incident thereon. Responsive to the absorbed light from the LED 953 and environmental influences in the area surrounding the package 950 on the luminescent material 957, the luminescent material 957 emits light at an emission wavelength $\lambda_2$, where $\lambda_1$ and $\lambda_2$ are different wavelengths or wavelength ranges.

The PD 954 with the filter 955 disposed on its upper surface acts as a wavelength selective light detector for detecting light within a predetermined wavelength range. In accordance with an illustrative embodiment, the wavelength selective light detector detects light that is emitted by the luminescent material 957 in the presence of one or more environmental influences. The environmental influences may affect the intensity of the light emitted by the luminescent material 957. In particular, the degree to which the environmental influences are present, e.g., the concentration of the environmental influences, in the area surrounding the package 950 may affect the intensity of the light emitted by the luminescent material. In accordance with an illustrative embodiment, if light within the predetermined wavelength range is not detected by the PD 954, this may be indicative of a high concentration or degree of presence of the one or more particular environmental influences on the luminescent material 957. For example, if there is a high concentration of a particular gas in the area surrounding the package 950, and the gas strongly affects the emission of light by the luminescent material 957, the luminescent material 957 may not emit light of an intensity detectable by the PD 954.

It should be noted that the invention has been described with reference to illustrative, or exemplary, embodiments in order to demonstrate the principles and concepts of the invention. As will be understood by those of skill in the art, the invention is not limited to the illustrative embodiments described herein. For example, the configuration of elements and materials that allow for sensing of luminescent activity are not limited to the configurations and materials that have been described herein. Persons skilled in the art will understand, in view of the description provided herein, that a variety of configurations and materials can be used to sense luminescent activity. Persons skilled in the art will understand the manner in which these and other modifications may be made to the embodiments described herein and that all such modifications are within the scope of the invention.

What is claimed is:

1. A compact system, comprising:
   an optoelectronic module including a light source configured to emit light at a predetermined wavelength and a wavelength selective light detector configured to detect light within a predetermined wavelength range; and
   a luminescence module comprising multiple luminescent materials, wherein the luminescence module is configured to emit light at multiple variable wavelengths that are different from the predetermined wavelength responsive to the light emitted by the light source that is incident on each respective luminescent material and depending upon at least one environmental influence on each respective luminescent material, an intensity of the light emitted by the luminescence module depends upon at least one environmental influence on the luminescent material in an area surrounding the compact system, and the wavelength selective light detector is configured to detect the light emitted by the luminescence module that is within a predetermined wavelength range and to emit a value corresponding to the intensity of the light emitted by the luminescence module.

2. The compact system of claim 1, wherein the value includes at least one of a voltage value and a current value.

3. The compact system of claim 1, wherein an alarm is generated responsive to the emitted value meeting a predetermined threshold.

4. The compact system of claim 1, wherein the optoelectronic module includes multiple wavelength selective light detectors, each respective wavelength selective light detector configured to detect light of a wavelength that is within a predetermined wavelength range that is specific to the respective wavelength selective light detector.

5. The compact system of claim 1, wherein the optoelectronic module includes multiple light sources, each respective light source configured to emit light at a respective predetermined wavelength.

6. The compact system of claim 1, wherein the light source is configured to periodically emit the light at the predetermined wavelength, the luminescence module is configured to periodically emit the light at a variable wavelength responsive to the light periodically emitted by the light source that is incident upon the luminescent material, and a variation in a phase shift between the light periodically emitted by the light source and the light periodically emitted by the luminescence module over time is indicative of at least one environmental influence on the luminescent material.

7. A compact device, comprising:
   a light source configured to emit light at a predetermined wavelength; and
   a wavelength selective light detector configured to detect light within a predetermined wavelength range, wherein a luminescence module comprising multiple luminescent material is configured to emit light at multiple variable wavelengths that are different from the predetermined wavelength responsive to the light emitted by the light source that is incident on each respective luminescent material, an intensity of the light emitted by the luminescence module depends upon at least one environmental influence on each respective luminescent material in an area surrounding the compact device, and the wavelength selective light detector is configured to detect the light emitted by the luminescence module that is within a predetermined wavelength range and to emit a value corresponding to the intensity of the light emitted by the luminescence module.

8. The compact device of claim 7, wherein the value includes at least one of a voltage value and a current value.

9. The compact device of claim 7, wherein an alarm is generated responsive the emitted value meeting a predetermined threshold.

10. The compact device of claim 7, further comprising multiple wavelength selective light detectors, each respective wavelength selective light detector configured to detect light of a wavelength that is within a predetermined wavelength range that is specific to the respective wavelength selective light detector.

11. The compact device of claim 7, further comprising multiple light sources, each respective light source configured to emit light at a respective predetermined wavelength.

12. The compact device of claim 7, wherein the light source is configured to periodically emit the light at the predetermined wavelength, the luminescence module is configured to periodically emit the light at a variable wavelength responsive to the light periodically emitted by the light source that is incident upon the luminescent material, and a variation in a phase shift between the light emitted by the light source and the light emitted by the luminescence module over time is indicative of at least one environmental influence on the luminescent material.

13. A method, comprising:
  emitting, by a light source, light at a predetermined wavelength;
  absorbing, by a luminescence module comprising multiple luminescent materials, the light emitted by the light source that is incident on the respective luminescent material;
  emitting, by the luminescence module, light at multiple variable wavelengths that are different from the predetermined wavelength responsive to the light emitted by the light source that is incident on each respective luminescent material and depending upon at least one environmental influence on each respective luminescent material;
  detecting, by a wavelength selective light detector, the light emitted by the luminescence module that is within a predetermined wavelength range; and
  emitting a value corresponding to the intensity of the light emitted by the luminescence module, wherein the light source, the luminescence module, and the wavelength selective light detector are included in a compact device, and an intensity of the light emitted by the luminescence module depends upon at least one environmental influence on the luminescent material in an area surrounding the compact device.

14. The method of claim 13, wherein the value includes at least one of a voltage value and a current value.

15. The method of claim 13, wherein an alarm is generated responsive the emitted value meeting a predetermined threshold.

16. The method of claim 13, wherein there are multiple wavelength selective light detectors, each respective wavelength selective light detector detecting light of a wavelength that is within a predetermined wavelength range that is specific to the respective wavelength selective light detector.

17. The method of claim 13, wherein there are multiple light sources, each respective light source emitting light at a respective predetermined wavelength.

18. The method of claim 13, wherein the light source periodically emits the light at the predetermined wavelength, and the luminescence module periodically emits the light at the variable wavelength responsive to the light periodically emitted by the light source that is incident upon the luminescent material, and wherein a variation in a phase shift between the light periodically emitted by the light source and the light periodically emitted by the luminescence module over time is indicative of at least one environmental influence on the luminescent material.

19. A compact system, comprising:
  an optoelectronic module including a light source configured to emit light at a predetermined wavelength and multiple wavelength selective light detectors, each respective wavelength selective light detector configured to detect light of a wavelength that is within a predetermined wavelength range that is specific to the respective wavelength selective light detector; and
  a luminescence module including a luminescent material, wherein the luminescence module is configured to emit light at a variable wavelength that is different from the predetermined wavelength responsive to the light emitted by the light source that is incident on the luminescent material, an intensity of the light emitted by the luminescence module depends upon at least one environmental influence on the luminescent material in an area surrounding the compact system, and the wavelength selective light detector is configured to detect the light emitted by the luminescence module that is within a predetermined wavelength range and to emit a value corresponding to the intensity of the light emitted by the luminescence module.

20. A compact system, comprising:
  an optoelectronic module including multiple light sources and a wavelength selective light detector, each respective light source configured to emit light at a respective predetermined wavelength, the wavelength selective light detector being configured to detect light within a predetermined wavelength range; and
  a luminescence module including a luminescent material, wherein the luminescence module is configured to emit light at a variable wavelength that is different from the predetermined wavelength responsive to the light emitted by the light source that is incident on the luminescent material, an intensity of the light emitted by the luminescence module depends upon at least one environmental influence on the luminescent material in an area surrounding the compact system, and the wavelength selective light detector is configured to detect the light emitted by the luminescence module that is within a predetermined wavelength range and to emit a value corresponding to the intensity of the light emitted by the luminescence module.

21. A compact system, comprising:
  an optoelectronic module including a light source configured to periodically emit light at a predetermined wavelength and a wavelength selective light detector configured to detect light within a predetermined wavelength range; and
  a luminescence module including a luminescent material, wherein the luminescence module is configured to periodically emit light at a variable wavelength that is different from the predetermined wavelength responsive to the light periodically emitted by the light source that is incident on the luminescent material, an intensity of the light emitted by the luminescence module depends upon at least one environmental influence on the luminescent material in an area surrounding the compact system, and the wavelength selective light detector is configured to detect the light emitted by the luminescence module that is within a predetermined wavelength range and to emit a value corresponding to the intensity of the light emitted by the luminescence module, and wherein a variation in a phase shift between the light periodically emitted by the light source and the light periodically emitted by the luminescence module over time is indicative of at least one environmental influence on the luminescent material.

22. A compact device, comprising:
  a light source configured to emit light at a predetermined wavelength; and
  multiple wavelength selective light detectors, each respective wavelength selective light detector configured to detect light of a wavelength that is within a predetermined wavelength range that is specific to the respective wavelength selective light detector, wherein a luminescence module including a luminescent material is configured to emit light at a variable wavelength that is different from the predetermined wavelength responsive to the light emitted by the light source that is incident on the luminescent material, an intensity of the light emitted by the luminescence module depends upon at least one environmental influence on the luminescent material in an area surrounding the compact device, and the wavelength selective light detector is configured to detect the light emitted by the luminescence module that is within a predetermined wavelength range and to emit a value corresponding to the intensity of the light emitted by the luminescence module.

23. A compact device, comprising:
multiple light sources, each respective light source configured to emit light at a respective predetermined wavelength; and
a wavelength selective light detector configured to detect light within a predetermined wavelength range, wherein a luminescence module including a luminescent material is configured to emit light at a variable wavelength that is different from the predetermined wavelength responsive to the light emitted by the light source that is incident on the luminescent material, an intensity of the light emitted by the luminescence module depends upon at least one environmental influence on the luminescent material in an area surrounding the compact device, and the wavelength selective light detector is configured to detect the light emitted by the luminescence module that is within a predetermined wavelength range and to emit a value corresponding to the intensity of the light emitted by the luminescence module.

24. A compact device, comprising:
a light source configured to periodically emit the light at the predetermined wavelength; and
a wavelength selective light detector configured to detect light within a predetermined wavelength range, wherein a luminescence module including a luminescent material is configured to periodically emit light at a variable wavelength that is different from the predetermined wavelength responsive to the light periodically emitted by the light source that is incident upon the luminescent material, an intensity of the light emitted by the luminescence module depends upon at least one environmental influence on the luminescent material in an area surrounding the compact device, and the wavelength selective light detector is configured to detect the light emitted by the luminescence module that is within a predetermined wavelength range and to emit a value corresponding to the intensity of the light emitted by the luminescence module, and wherein a variation in a phase shift between the light emitted by the light source and the light emitted by the luminescence module over time is indicative of at least one environmental influence on the luminescent material.

25. A method, comprising:
emitting, by a light source, light at a predetermined wavelength;
absorbing, by a luminescence module including a luminescent material, the light emitted by the light source that is incident on the luminescent material;
emitting, by the luminescence module, light at a variable wavelength that is different from the predetermined wavelength;
detecting, by multiple wavelength selective light detectors, light of a wavelength that is within a predetermined wavelength range that is specific to the respective wavelength selective light detector; and
emitting a value corresponding to the intensity of the light emitted by the luminescence module, wherein the light source, the luminescence module, and the wavelength selective light detector are included in a compact device, and an intensity of the light emitted by the luminescence module depends upon at least one environmental influence on the luminescent material in an area surrounding the compact device.

26. A method, comprising:
emitting, by multiple light sources, light at respective predetermined wavelengths;
absorbing, by a luminescence module including a luminescent material, the light emitted by the light source that is incident on the luminescent material;
emitting, by the luminescence module, light at a variable wavelength that is different from the predetermined wavelength;
detecting, by a wavelength selective light detector, the light emitted by the luminescence module that is within a predetermined wavelength range; and
emitting a value corresponding to the intensity of the light emitted by the luminescence module, wherein the light source, the luminescence module, and the wavelength selective light detector are included in a compact device, and an intensity of the light emitted by the luminescence module depends upon at least one environmental influence on the luminescent material in an area surrounding the compact device.

27. A method, comprising:
periodically emitting, by a light source, light at a predetermined wavelength;
absorbing, by a luminescence module including a luminescent material, the light emitted by the light source that is incident on the luminescent material;
periodically emitting, by the luminescence module, light at a variable wavelength that is different from the predetermined wavelength responsive to the light periodically emitted by the light source that is incident upon the luminescent material, and wherein a variation in a phase shift between the light periodically emitted by the light source, and wherein the light periodically emitted by the luminescence module over time is indicative of at least one environmental influence on the luminescent material;
detecting, by a wavelength selective light detector, the light emitted by the luminescence module that is within a predetermined wavelength range; and
emitting a value corresponding to the intensity of the light emitted by the luminescence module, wherein the light source, the luminescence module, and the wavelength selective light detector are included in a compact device, and an intensity of the light emitted by the luminescence module depends upon at least one environmental influence on the luminescent material in an area surrounding the compact device.

* * * * *